United States Patent
Zack et al.

(10) Patent No.: US 9,539,239 B1
(45) Date of Patent: Jan. 10, 2017

(54) COMPOSITIONS AND METHODS FOR TREATMENT OF NEURODEGENERATIVE DISEASE

(71) Applicants: Donald Jeffrey Zack, Baltimore, MD (US); Thomas Bannister, Palm Beach Gardens, FL (US); Tomas Vojkovsky, Palm Beach Gardens, FL (US); Zhiyong Yang, San Diego, CA (US); Cynthia Berlinicke, Baltimore, MD (US)

(72) Inventors: Donald Jeffrey Zack, Baltimore, MD (US); Thomas Bannister, Palm Beach Gardens, FL (US); Tomas Vojkovsky, Palm Beach Gardens, FL (US); Zhiyong Yang, San Diego, CA (US); Cynthia Berlinicke, Baltimore, MD (US)

(*) Notice: Subject to any disclaimer, the term of this patent is extended or adjusted under 35 U.S.C. 154(b) by 0 days.

(21) Appl. No.: 14/886,938

(22) Filed: Oct. 19, 2015

Related U.S. Application Data

(63) Continuation of application No. 13/636,415, filed as application No. PCT/US2011/029689 on Mar. 23, 2011, now Pat. No. 9,162,981.

(60) Provisional application No. 61/316,465, filed on Mar. 23, 2010.

(51) Int. Cl.
*A61K 9/00* (2006.01)
*A61K 31/404* (2006.01)
*A61K 45/06* (2006.01)
*C07D 403/06* (2006.01)

(52) U.S. Cl.
CPC ............ *A61K 31/404* (2013.01); *A61K 45/06* (2013.01); *C07D 403/06* (2013.01)

(58) Field of Classification Search
CPC .................................................. A61K 31/404
See application file for complete search history.

(56) References Cited

U.S. PATENT DOCUMENTS 7,256,189 B2   8/2007  Guan et al.

FOREIGN PATENT DOCUMENTS

WO    2005047273 A1    5/2005
WO    2010017541 A2    2/2010

OTHER PUBLICATIONS

Qu et al., Mechanism of retinal ganglion cell injury and defense in glaucoma. Experimental Eye Research 2010, 91, 48-53.
Vasudevan et al., Neuroprotection in glaucoma. Indian Journal of Ophthalmology 2011, 59, S102-S113.
Shafer, S., Kolkhof, P. Failure is an option: learning from unsuccessful proof-of-concept trials. Drug Discovery Today. Nov. 2008, 13, 913-916.
Horig, H., Pullman, W. From bench to clinic and back: Perspective on the 1st IQPC Translational Research conference.Journal of Translational Medicine. Dec. 2004, 2, 44.
CAPLUS printout of Gao et al., Study on indol-2-ones as PDGF-Rbeta kinase inhibitors. Lanzhou Daxue Xuebao, Ziran Kexueban. 2004, 40, 56-60.
CAPLUS printout of Kumar et al., QSAR studies of amino propyl tetrahydro indole based indolin-2-ones as potent inhibitor of Src tyrosine kinase. Journal of Teaching and Research in Chemistry. 2004, 11, 20-24.
Johnson, K. et al., Journal of Neurochemistry, 2005, vol. 93, No. 3, pp. 538-548.
Non-Final Office Action dated Jun. 20, 2014 for the U.S. Appl. No. 13/636,415.
Final Office Action dated Jan. 29, 2015 for the U.S. Appl. No. 13/636,415.
International Search Report dated Dec. 28, 2011 for PCT International Application No. PCT/US2011/029689.

*Primary Examiner* — Paul Dickinson
(74) *Attorney, Agent, or Firm* — Ward and Smith, P.A.; Jeffrey W. Childers

(57) ABSTRACT

Compounds, compositions, kits and methods for treating conditions related to neurodegeneration or ocular disease, are disclosed.

25 Claims, No Drawings

COMPOSITIONS AND METHODS FOR TREATMENT OF NEURODEGENERATIVE DISEASE

CROSS-REFERENCE TO RELATED APPLICATIONS

This application is a continuation application of U.S. patent application Ser. No. 13/636,415, filed May 9, 2013, which is a 35 U.S.C. §371 National Stage Entry of International Application No. PCT/US2011/29689 having an international filing date of Mar. 23, 2011, which claims the benefit of priority to U.S. Provisional Application No. 61/316,465, filed Mar. 23, 2010, the content of each of the aforementioned applications is herein incorporated by reference in its entirety.

STATEMENT OF RIGHTS TO INVENTIONS MADE UNDER FEDERALLY SPONSORED RESEARCH

This work was supported at least in part by NEI/NIH grant no. 5R21EY019737-0109. The government has certain rights in the invention.

BACKGROUND OF THE INVENTION

Neurodegenerative disorders afflict numerous patients throughout the world, and treatments are often unsatisfactory. For example, glaucoma (a disease or condition that results in damage to the optic nerve) is a major cause of vision loss and blindness, especially in the elderly. Although various treatments for glaucoma exist, many such treatments are of limited efficacy and/or have significant side effects. For example, while reduction of intraocular pressure, generally through pharmacologic or surgical intervention, is presently the mainstay of glaucoma therapy, such therapies are often only partially effective and generally cannot restore neuronal cell function once such function has been lost. Thus, new methods for treatment of ocular and/or neurodegenerative disorders or diseases, including glaucoma, are needed.

SUMMARY OF THE INVENTION

The invention relates generally to the discovery that certain compounds (including protein kinase inhibitors (e.g., FLT3 inhibitors)) can promote the survival and/or neurite outgrowth of retinal ganglion cells (RGCs).

In one aspect, the invention provides a compound represented by Formula I:

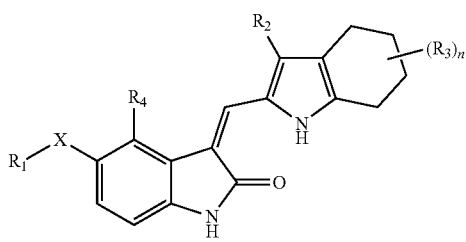

(I)

wherein:
X is C(O) or S(O);
If X is S(O), then $R_1$ is substituted or unsubstituted $C_1$-$C_6$ alkyl, $C_3$-$C_6$ cycloalkyl or allyl; or
if X is C(O), then $R_1$ is substituted or unsubstituted $C_1$-$C_6$ alkyl, $C_3$-$C_6$ cycloalkyl, allyl or —N($R_5R_6$);
$R_2$ is H or substituted or unsubstituted $C_1$-$C_6$ alkyl, $C_3$-$C_6$ cycloalkyl or allyl;
$R_3$ is selected, independently for each occurrence, from the group consisting of substituted or unsubstituted $C_1$-$C_6$ alkyl, $C_3$-$C_6$ cycloalkyl, allyl, substituted or unsubstituted $C_1$-$C_6$ alkoxy, aryl, cyano, halogen, hydroxy, oxo, amino, or —C(O)—$R_a$, in which $R_a$ is substituted or unsubstituted $C_1$-$C_6$ alkyl, $C_3$-$C_6$ cycloalkyl, allyl, substituted or unsubstituted $C_1$-$C_6$ alkoxy, aryl, or amino;
$R_4$ is H, substituted or unsubstituted $C_1$-$C_6$ alkyl, $C_3$-$C_6$ cycloalkyl or allyl;
$R_5$ and $R_6$ are each independently H, substituted or unsubstituted $C_1$-$C_6$ alkyl, $C_3$-$C_6$ cycloalkyl or allyl; or $R_5$ and $R_6$, taken together with the nitrogen atom to which they are attached, form a 4-10-membered heterocyclic ring; and
n is 0 to 4;
or a pharmaceutically acceptable salt or solvate thereof.

In another aspect, the invention provides a compound represented by Formula II:

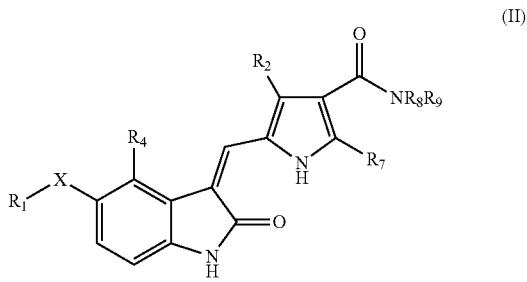

(II)

wherein:
X is C(O) or S(O);
If X is S(O), then $R_1$ is substituted or unsubstituted $C_1$-$C_6$ alkyl, $C_3$-$C_6$ cycloalkyl or allyl; or
if X is C(O), then $R_1$ is substituted or unsubstituted $C_1$-$C_6$ alkyl, $C_3$-$C_6$ cycloalkyl, allyl or —N($R_5R_6$);
$R_2$ is H or substituted or unsubstituted $C_1$-$C_6$ alkyl, $C_3$-$C_6$ cycloalkyl or allyl;
$R_4$ is H or substituted or unsubstituted $C_1$-$C_6$ alkyl, $C_3$-$C_6$ cycloalkyl or allyl;
$R_5$ and $R_6$ are each independently H, methoxy, substituted or unsubstituted $C_1$-$C_6$ alkyl, $C_3$-$C_6$ cycloalkyl or allyl; or $R_5$ and $R_6$, taken together with the nitrogen atom to which they are attached, form a 4-10-membered heterocyclic ring;
$R_7$ is H or substituted or unsubstituted $C_1$-$C_6$ alkyl, $C_3$-$C_6$ cycloalkyl or allyl;
$R_8$ and $R_9$ are each independently H, substituted or unsubstituted $C_1$-$C_6$ alkyl, $C_3$-$C_6$ cycloalkyl or allyl; or $R_8$ and $R_9$, together with the nitrogen atom to which they are attached, form a 4-10-membered heterocyclic ring;
n is 0 to 4;
or a pharmaceutically acceptable salt or solvate thereof.

In certain embodiments of Formula I or Formula II, X is S(O).

In certain embodiments of Formula I or Formula II, $R_4$ is H or methyl.

In certain embodiments of Formula I or Formula II, $R_1$ is methyl or ethyl.

In certain embodiments of Formula I or Formula II, $R_2$ is methyl or ethyl.

In certain embodiments of Formula I, n is 1-4; or n is one or two. In certain embodiments, n is one or two and each $R_3$ is methyl. In certain embodiments of Formula I, n is at least 3, and two occurrences of $R_3$ are gem-dimethyl groups and one occurrence of $R_3$ is oxo.

In certain embodiments of Formula I or Formula II, X is C(O) and $R_1$ is —N($R_5R_6$). In certain embodiments, $R_5$ and $R_6$ are each independently unsubstituted $C_1$-$C_6$ alkyl. In certain embodiments $R_5$ and $R_6$ are taken together with the nitrogen atom to which they are attached to form a 4-10-membered heterocyclic ring.

In certain embodiments of Formula II, $R_8$ is H and $R_9$ is —(CH$_2$)$_2$N(ethyl)$_2$.

In certain embodiments of Formula I or Formula II, the compound is selected from the group consisting of:

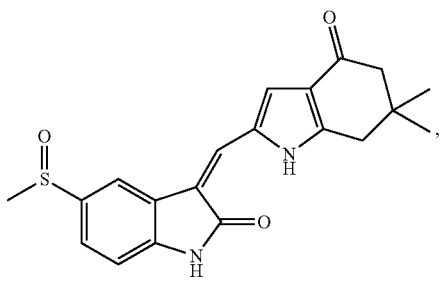

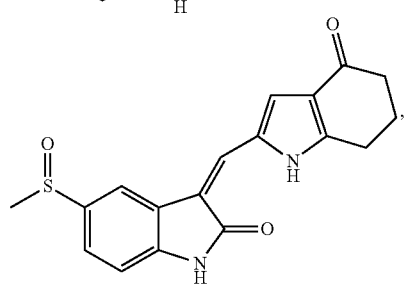

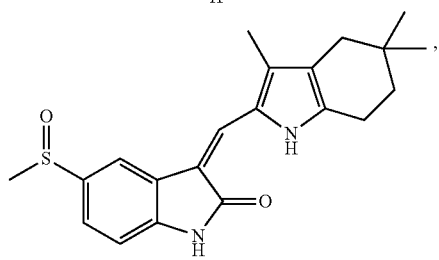

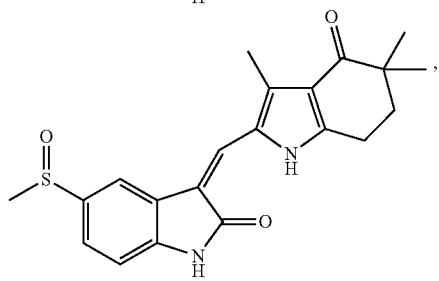

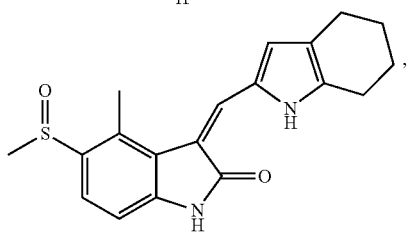

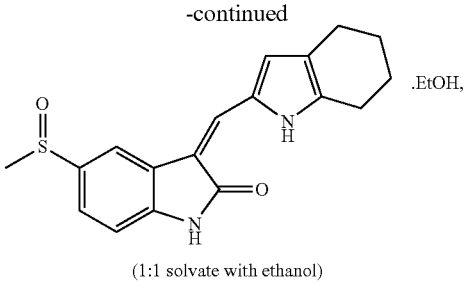

(1:1 solvate with ethanol)

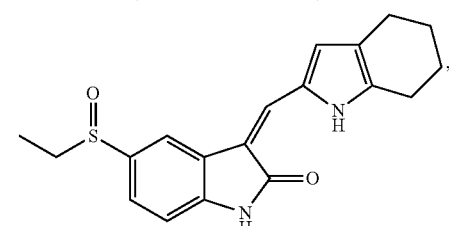

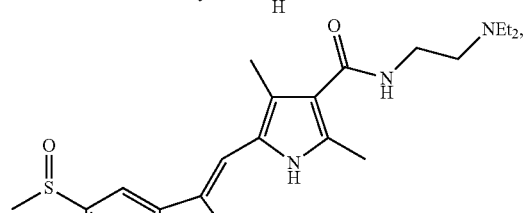

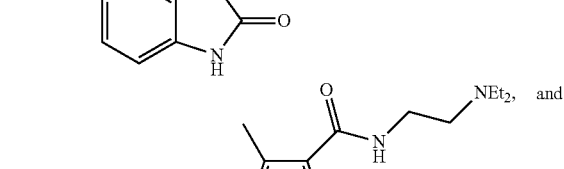

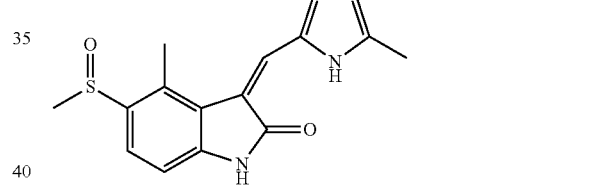

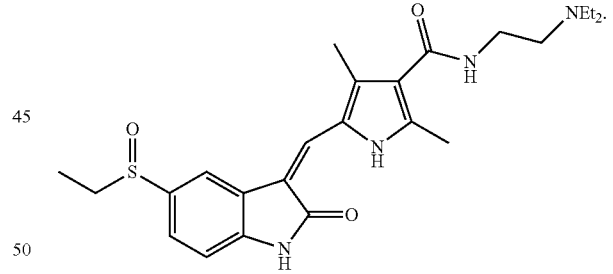

In another aspect, the invention provides a method of treating or preventing a neurodegenerative disease or disorder, the method comprising administering to a subject in need thereof an effective amount of a compound of Formula I or II, or a pharmaceutically acceptable salt thereof, to the subject, thereby treating or preventing the neurodegenerative disease or disorder.

In certain embodiments, the neurodegenerative disease or disorder is glaucoma. In certain embodiments, the neurodegenerative disease or disorder is glaucoma that is not neovascular glaucoma.

In certain embodiments, the step of administering the compound includes administering the compound in a pharmaceutically acceptable composition.

In certain embodiments, the subject is a mammal. In certain embodiments, the subject is a human.

In certain embodiments, the method further comprises the step of monitoring the subject to determine the efficacy of treatment.

In another aspect, the invention provides a method for treating or preventing neuronal cell loss in a subject in need of such treatment, the method comprising administering to the subject an effective amount of a compound of Formula I or II, or a pharmaceutically acceptable salt thereof, thereby treating or preventing neuronal cell loss in the subject.

In certain embodiments of the methods, the effective amount of the compound, or a pharmaceutically acceptable salt thereof, is in a range of 0.0001 to about 100 mg per kilogram of body weight per day.

In certain embodiments of the methods, the compound, or a pharmaceutically acceptable salt thereof, is administered to the subject by a method selected from the group consisting of: oral, topical, parenteral, and systemic.

In certain embodiments of the methods, an additional therapeutic agent is administered to the subject. In certain embodiments, the additional therapeutic agent is selected from the group consisting of beta-blockers, alpha-agonists, carbonic anhydrase inhibitors, prostaglandins or prostaglandin analogs, miotic or cholinergic agents, epinephrine compounds, forskolin, or neuroprotective compounds.

In another aspect, the invention provides a method for treating or preventing neuronal cell death, the method comprising contacting a neuronal cell with an effective amount of a compound of Formula I or II, or a pharmaceutically acceptable salt thereof, thereby treating or preventing neuronal cell death.

In another aspect, the invention provides a method of treating or preventing NMDA-induced excitotoxicity, the method comprising administering to a subject in need thereof an effective amount of a compound of Formula I or II, or a pharmaceutically acceptable salt thereof, thereby treating or preventing the neurodegenerative disease or disorder.

In another aspect, the invention provides a method of stimulating growth or regeneration of neurites, the method comprising administering to a subject in need thereof an effective amount of a compound of Formula I or II, or a pharmaceutically acceptable salt thereof, thereby stimulating growth or regeneration of neurites.

In another aspect, the invention provides a method of preventing apoptosis of neuronal cells, the method comprising administering to a subject in need thereof an effective amount of a compound of Formula I or II, or a pharmaceutically acceptable salt thereof, thereby preventing apoptosis of neuronal cells.

In another aspect, the invention provides a method of preventing cell death in a neuronal cell, the method comprising administering to a cell in need thereof an effective amount of a compound of Formula I or II, or a pharmaceutically acceptable salt thereof, thereby preventing cell death in the neuronal cell.

In another aspect, the invention provides a method of treating traumatic injury to a neuronal cell, the method comprising administering to a neuronal cell in need thereof an effective amount of a compound of Formula I or II, or a pharmaceutically acceptable salt thereof, thereby treating traumatic injury in the neuronal cell. In certain embodiments, the traumatic injury is an ischemic condition of the nervous system. In certain embodiments, the ischemic condition of the nervous system is stroke.

In another aspect, the invention provides a kit comprising a compound of Formula I or II, or a pharmaceutically acceptable salt thereof, in unit dosage form, together with instructions for using the compound, or a pharmaceutically acceptable salt thereof, for treating or preventing a neurodegenerative disease or disorder.

Other features and advantages of the invention will be apparent from the detailed description, and from the claims.

DETAILED DESCRIPTION OF THE INVENTION

The invention relates generally to the discovery that certain compounds, including compounds which can inhibit protein kinases such as FLT3, can promote the survival and/or neurite outgrowth of retinal ganglion cells (RGCs). In certain embodiments, a compound is used according to this invention to prevent the death of damaged neuronal cells. In other embodiments, a compound is used according to this invention to promote the growth or regeneration of all or part of a neuronal cell (e.g., growth of neurites such as axons, dendrites, and the like). The invention also relates to methods for treating neurodegenerative diseases and disorders by administration of such compounds.

The invention further relates to compounds and methods for treating or preventing neurodegenerative diseases and disorders by inhibiting the activity of an enzymes selected from the group consisting of JNK1-3, the MAP2Ks, TAK1, RIPK1-3, CDKs, MLCK, HPK1, RET, LCK, LRRK, GSK3, RAP, SRC kinases, STE20 kinases, and trkA, thereby treating or preventing the neurodegenerative disease or disorder.

Definitions

By the term "decrease" is meant inhibit, suppress, attenuate, diminish, arrest, or stabilize a symptom of a neurodegenerative disease or disorder.

By "neurodegenerative disease or disorder" is meant a disorder (including a neuropathy) associated with degeneration or dysfunction of neurons or other neural cells such as retinal ganglion cells. A neurodegenerative disease or disorder can be any disease or condition in which decreased function or dysfunction of neurons, or loss or neurons or other neural cells, can occur. Such conditions include, without limitation, glaucoma, and neurodegenerative disorders such as or associated with alcoholism, Alexander's disease, Alper's disease, Alzheimer's disease, amyotrophic lateral sclerosis (Lou Gehrig's Disease), ataxia telangiectasia, Batten disease (also known as Spielmeyer-Vogt-Sjogren-Batten disease), bovine spongiform encephalopathy (BSE), Canavan disease, Cockayne syndrome, corticobasal degeneration, Creutzfeldt-Jakob disease, diabetic neuropathy, frontotemporal lobar degeneration, Huntington's disease, HIV-associated dementia, Kennedy's disease, Krabbe's disease, Lewy body dementia, neuroborreliosis, Machado-Joseph disease (Spinocerebellar ataxia type 3), wet or dry macular degeneration, Multiple System Atrophy, multiple sclerosis, Niemann Pick disease, Parkinson's disease, Pelizaeus-Merzbacher Disease, photoreceptor degenerative diseases such as retinitis pigmentosa and associated diseases, Pick's disease, primary lateral sclerosis, prion diseases, Progressive Supranuclear Palsy, Refsum's disease, Sandhoffs disease, Schilder's disease, subacute combined degeneration of spinal cord secondary to pernicious anemia, Spielmeyer-Vogt-Sjogren-Batten disease (also known as Batten disease), spinocerebellar ataxia (multiple types with varying characteristics), spinal muscular atrophy, Steele-Richardson-Olszewski disease, and tabes dorsalis. Traumatic injury or other damage to neuronal cells (e.g., trauma due to accident, blunt-force injury, gunshot injury, spinal cord injury, ischemic conditions of the nervous system such as stroke, cell damage due to aging or oxidative stress, and the like) is also intended to be included within the language "neurodegenerative disease or disorder". In certain embodiments, the neurodegenerative disease or disorder is a disease or disorder that is not associated with excessive angiogenesis, for example, glaucoma that is not neovascular glaucoma.

The term "inhibit" or "inhibits" means to decrease, suppress, attenuate, diminish, arrest, or stabilize the development or progression of a disease or disorder, or the activity of a biological pathway, e.g., by at least 10, 20, 30, 40, 50, 60, 70, 80, 90, 95, 98, or 99% compared to an untreated control subject, cell, or biological pathway.

The term "$IC_{50}$" means the dose of a drug which is half the maximal inhibitory concentration.

The term "neurite" means a projection from the cell body of a neuron including, e.g., an axon or a dendrite.

The term "subject" refers to human or non-human animals, typically mammalian animals, such as primates (humans, apes, gibbons, chimpanzees, orangutans, macaques), domestic animals (dogs and cats), farm animals (horses, cattle, goats, sheep, pigs) and experimental animals (mouse, rat, rabbit, guinea pig). Subjects include animal disease models (e.g., rats or mice used in experiments, e.g., optic crush experiments).

The phrases "parenteral administration" and "administered parenterally" as used herein means modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "FLT3" refers to the receptor tyrosine kinase "Fms-like Tyrosine Kinase-3", also known as FLK2 (Fetal Liver Kinase-2) or STK1 (human Stem Cell Kinase-1). FLT3 belongs to the Class-III RTK (Receptor Tyrosine Kinase) family. In certain embodiments, FLT3 refers to a human FLT3.

The term "therapeutically effective amount" refers to an amount sufficient to produce the desired effect, e.g., to reduce or ameliorate the severity, duration, progression, or onset of a disease, condition, or disorder (e.g., a disease, condition, or disorder related to loss of neuronal cells or cell function), or one or more symptoms thereof; prevent the advancement of a disease, condition, or disorder; cause the regression of a disease, condition, or disorder; prevent the recurrence, development, onset or progression of a symptom associated with a disease, condition, or disorder; or enhance or improve the prophylactic or therapeutic effect(s) of another therapy. An effective amount of a compound according to this invention can range from, e.g., about 0.001 mg/kg to about 1000 mg/kg, or in certain embodiments, about 0.01 mg/kg to about 100 mg/kg, or in certain embodiments, about 0.1 mg/kg to about 50 mg/kg. Effective doses will also vary, as recognized by those skilled in the art, depending on the disorder treated, route of administration, excipient usage, the age and sex of the subject, and the possibility of co-usage with other therapeutic treatments such as use of other agents. It will be appreciated that an amount of a compound required for achieving, e.g., neuroprotective activity, may be different from the amount of compound effective for another purpose (e.g., antineoplastic activity).

The term "$ED_{50}$" means the dose of a drug which produces 50% of its maximum response or effect. Alternatively, the dose which produces a pre-determined response in 50% of test subjects or preparations.

The term "$LD_{50}$" means the dose of a drug which is lethal in 50% of test subjects.

The term "therapeutic index" refers to the therapeutic index of a drug defined as $LD_{50}/ED_{50}$.

The term "treatment" is intended to encompass also prophylaxis, therapy and cure.

As used herein, the term an "aromatic ring" or "aryl" means a monocyclic or polycyclic-aromatic ring or ring radical comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or optionally is substituted with one or more substituents (including without limitation alkyl (preferably, lower alkyl or alkyl substituted with one or more halo), hydroxy, alkoxy (preferably, lower alkoxy), alkylthio, cyano, halo, amino, and nitro. In certain embodiments, the aryl group is a monocyclic ring, wherein the ring comprises 6 carbon atoms.

As used herein, the term "alkyl" means a saturated straight chain or branched non-cyclic hydrocarbon typically having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. Alkyl groups included in compounds of this invention may be unsubstituted, or optionally substituted with one or more substituents, such as amino, alkylamino, alkoxy, alkylthio, oxo, halo, acyl, nitro, hydroxyl, cyano, aryl, alkylaryl, aryloxy, arylthio, arylamino, carbocyclyl, carbocyclyloxy, carbocyclylthio, carbocyclylamino, heterocyclyl, heterocyclyloxy, heterocyclylamino, heterocyclylthio, and the like. Lower alkyls having from 1 to 6 carbon atoms in the straight or branched chain are typically preferred for the compounds of this invention.

Alkoxy is —O-alkyl.

Halogen means F, Cl, Br, or I.

Compounds

In certain embodiments, the compound is a receptor tyrosine kinase inhibitor. In certain embodiments, the compound is an FLT3 inhibitor. The term "FLT3 inhibitor", as used herein, refers to a compound having partial or total FLT3-inhibitory activity at a therapeutically relevant dose. Such a compound can be a selective inhibitor of FLT3 (i.e., a compound that inhibits FLT3 but has relatively little inhibition of other receptor tyrosine kinases).

It has been reported that selective or non-selective FLT3 inhibitors include sunitinib, soratinib, lestaurtinib, bis-(5-hydroxy-1H-indol-2-yl)methanone, and (5-phenyl-thiazol-2-yl)-(4-(2-pyrrolidin-1-yl-ethoxy)-phenyl)-amine (see, e.g., PCT Publication No. WO2005/047273, incorporated herein by reference). Sunitinib (N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide, is a receptor tyrosine kinase (RTK) inhibitor approved by the FDA and marketed for treatment of cancers. Sunitinib has been reported to be useful for neuroprotection and treatment of neurodegenerative disorders (see, e.g., PCT Patent Publication No. WO 2010/017541, incorporated herein by reference). For additional examples of analogs or derivatives of sunitinib and related compounds, see, e.g., U.S. Pat. Nos. 6,573,293, 7,125,905, and 7,211,600, incorporated herein by reference.

In one aspect, the invention provides a compound represented by Formula I:

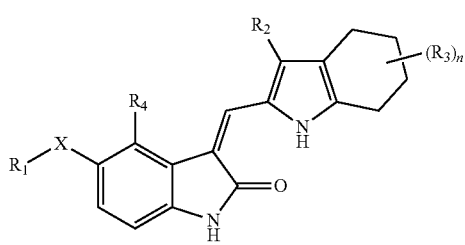

wherein:

X is C(O) or S(O);

If X is S(O), then $R_1$ is substituted or unsubstituted $C_1$-$C_6$ alkyl, $C_3$-$C_6$ cycloalkyl or allyl; or if X is C(O), then $R_1$ is substituted or unsubstituted $C_1$-$C_6$ alkyl, $C_3$-$C_6$ cycloalkyl, allyl or —N($R_5R_6$);

$R_2$ is H or substituted or unsubstituted $C_1$-$C_6$ alkyl, $C_3$-$C_6$ cycloalkyl or allyl;

$R_3$ is selected, independently for each occurrence, from the group consisting of substituted or unsubstituted $C_1$-$C_6$ alkyl, $C_3$-$C_6$ cycloalkyl, allyl, substituted or unsubstituted $C_1$-$C_6$ alkoxy, aryl, cyano, halogen, hydroxy, oxo, amino, or —C(O)—$R_a$, in which $R_a$ is substituted or unsubstituted $C_1$-$C_6$ alkyl, $C_3$-$C_6$ cycloalkyl, allyl, substituted or unsubstituted $C_1$-$C_6$ alkoxy, aryl, or amino;

$R_4$ is H, substituted or unsubstituted $C_1$-$C_6$ alkyl, $C_3$-$C_6$ cycloalkyl or allyl;

$R_5$ and $R_6$ are each independently H, substituted or unsubstituted $C_1$-$C_6$ alkyl, $C_3$-$C_6$ cycloalkyl or allyl; or $R_5$ and $R_6$, taken together with the nitrogen atom to which they are attached, form a 4-10-membered heterocyclic ring; and n is 0 to 4;

or a pharmaceutically acceptable salt or solvate thereof.

In another aspect, the invention provides a compound represented by Formula II:

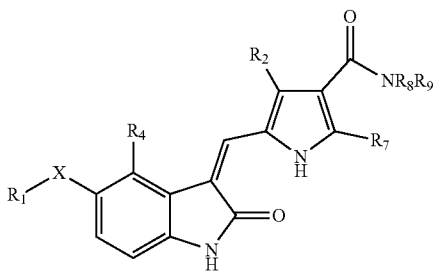

wherein:

X is C(O) or S(O);

If X is S(O), then $R_1$ is substituted or unsubstituted $C_1$-$C_6$ alkyl, $C_3$-$C_6$ cycloalkyl or allyl; or if X is C(O), then $R_1$ is substituted or unsubstituted $C_1$-$C_6$ alkyl, $C_3$-$C_6$ cycloalkyl, allyl or —N($R_5R_6$);

$R_2$ is H or substituted or unsubstituted $C_1$-$C_6$ alkyl, $C_3$-$C_6$ cycloalkyl or allyl;

$R_4$ is H or substituted or unsubstituted $C_1$-$C_6$ alkyl, $C_3$-$C_6$ cycloalkyl or allyl;

$R_5$ and $R_6$ are each independently H, methoxy, substituted or unsubstituted $C_1$-$C_6$ alkyl, $C_3$-$C_6$ cycloalkyl or allyl; or $R_5$ and $R_6$, taken together with the nitrogen atom to which they are attached, form a 4-10-membered heterocyclic ring;

$R_7$ is H or substituted or unsubstituted $C_1$-$C_6$ alkyl, $C_3$-$C_6$ cycloalkyl or allyl;

$R_8$ and $R_9$ are each independently H, substituted or unsubstituted $C_1$-$C_6$ alkyl, $C_3$-$C_6$ cycloalkyl or allyl; or $R_8$ and $R_9$, together with the nitrogen atom to which they are attached, form a 4-10-membered heterocyclic ring;

n is 0 to 4;

or a pharmaceutically acceptable salt or solvate thereof. In certain embodiments of Formula II, the compound is not the compound of Example 26 herein.

In certain embodiments of Formula I or Formula II, X is S(O).

In certain embodiments of Formula I or Formula II, $R_4$ is H or methyl.

In certain embodiments of Formula I or Formula II, $R_1$ is methyl or ethyl.

In certain embodiments of Formula I or Formula II, $R_2$ is methyl or ethyl.

In certain embodiments of Formula I, n is 1-4; or n is one or two. In certain embodiments, n is one or two and each $R_3$ is methyl. In certain embodiments of Formula I, n is at least 3, and two occurrences of $R_3$ are gem-dimethyl groups and one occurrence of $R_3$ is oxo.

In certain embodiments of Formula I or Formula II, X is C(O) and $R_1$ is —N($R_5R_6$). In certain embodiments, $R_5$ and $R_6$ are each independently unsubstituted $C_1$-$C_6$ alkyl. In certain embodiments $R_5$ and $R_6$ are taken together with the nitrogen atom to which they are attached to form a 4-10-membered heterocyclic ring.

In certain embodiments of Formula II, $R_8$ is H and $R_9$ is —$(CH_2)_2$N(ethyl)$_2$.

In certain embodiments of Formula I or Formula II, the compound is selected from the group consisting of:

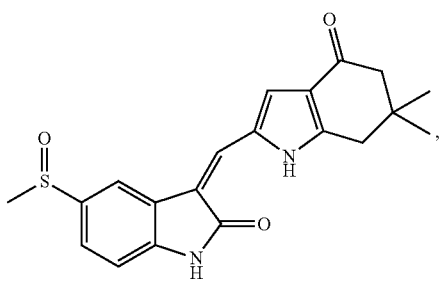

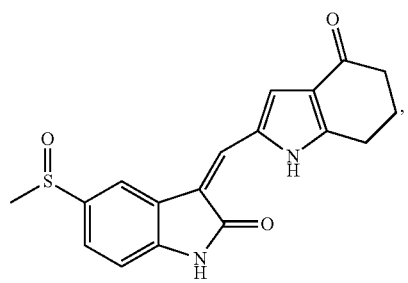

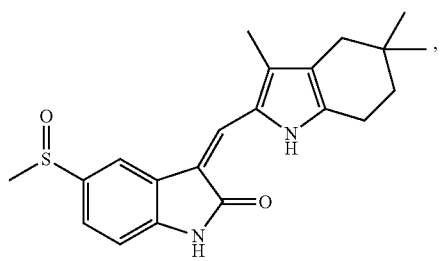

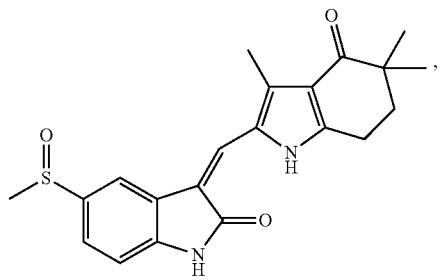

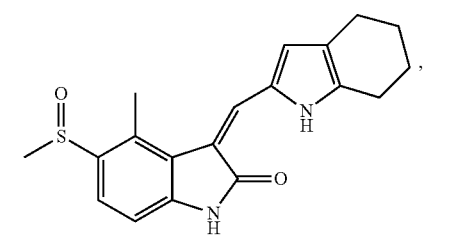
(1:1 solvate with ethanol)

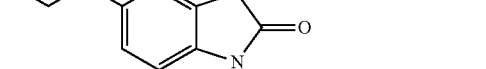

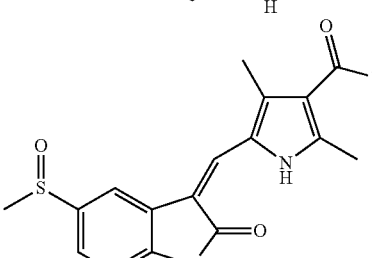

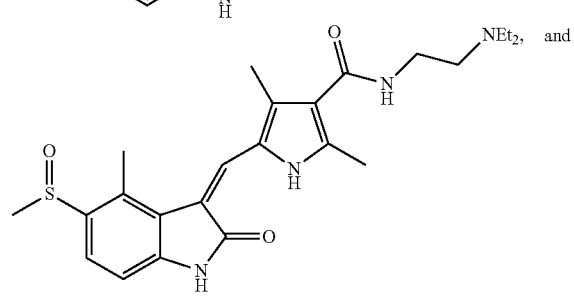

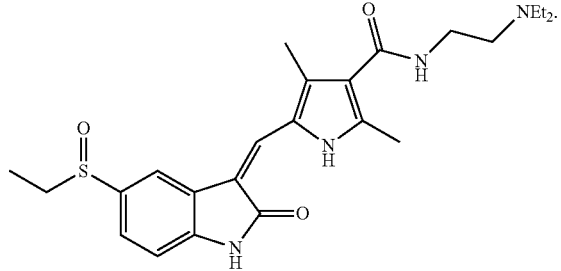

The compounds of the invention may contain one or more asymmetric centers and thus occur as racemates and racemic mixtures, single enantiomers, individual diastereomers and diastereomeric mixtures. In particular, the sulfoxide-containing compounds can include a chiral sulfur atom (a chiral sulfoxide). Such chiral sulfoxides can be prepared according to a variety of methods, some of which are known in the art (e.g., by asymmetric oxidation of a sulfide, or by separation of enantiomers by crystallization or chiral HPLC separation). All such isomeric forms of such compounds are expressly included in the present invention. In certain embodiments, a chiral sulfoxide compound is a single enantiomer that is substantially free of the antipode; in certain embodiments, the chiral sulfoxide moiety has the (S)-configuration; in other embodiments, the chiral sulfoxide moiety has the (R)-configuration.

The compounds of the invention may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds of the invention may also be represented in multiple tautomeric forms, in such instances, the invention expressly includes all tautomeric forms of the compounds described herein, even though only a single tautomeric form may be represented. All solvates, crystal forms and polymorphs of the compounds of the invention described herein are expressly included in the present invention.

Unless otherwise stated herein, compounds of the invention include the free base form and pharmaceutically acceptable salts, or of any stereoisomers thereof. Acid addition salts may be obtained by reaction of the base form with an appropriate acid. Appropriate acids comprise, for example, inorganic acids such as hydrohalic acids, e.g. hydrochloric or hydrobromic acid; sulfuric acid; nitric acid; phosphoric acid and the like; or organic acids such as, for example, acetic, propanoic, hydroxyacetic, 2-hydroxypropanoic, 2-oxopropanoic, ethanedioic, propanedioic, butanedioic, (Z)-butenedioic, (E)-butenedioic, 2-hydroxybutanedioic, 2,3-dihydroxybutanedioic, 2-hydroxy-1, 2, 3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

The compounds of the invention have now been found to have neuroprotective and neurite-stimulating activity (as measured in an in vitro assay), with an ability to protect retinal ganglion cells (RGCs). Without wishing to be bound by any theory, it is believed that the neuroprotective activity of the compounds of the invention may be useful in the treatment or prevention of glaucoma, optic nerve diseases, and other neurodegenerative disorders.

Screening Assays

The invention also relates to screening assays for identifying agents that have neuroprotectant activity. The screening method is also useful for identifying variants, binding or blocking agents, etc., which act as neuroprotectants.

Pharmaceutical Compositions

Pharmaceutical compositions and formulations of the present invention include pharmaceutical compositions of the neuroprotective compounds disclosed herein that can be administered to a mammal, and can also include veterinary compositions, e.g., pharmaceutical preparations of the subject compounds suitable for veterinary uses, e.g., for the treatment of livestock or domestic animals, e.g., dogs.

In one embodiment, the methods and compositions of the present invention comprise a compound of the invention and/or pharmaceutically acceptable salts thereof, such as the malate salt.

The invention provides for compositions comprising a compound according to the invention admixed with a physiologically compatible carrier. As used herein, "physiologically compatible carrier" refers to a physiologically acceptable diluents such as water, phosphate buffered saline, or saline, and further may include an adjuvant. Adjuvants such as incomplete Freund's adjuvant, aluminum phosphate, aluminum hydroxide, or alum are materials well known in the art.

Methods of introduction may be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a subject compound at a particular target site.

The preparations of the present invention may be given orally, parenterally, topically, or rectally. They are of course given by forms suitable for each administration route. For example, they are administered in tablets or capsule form, by injection (including intravitreal injection), inhalation, eye lotion, ointment, suppository, controlled release patch, etc. administration by injection, infusion or inhalation; topical by lotion or ointment; and rectal by suppositories.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the subject.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethyl cellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Additional ingredients may be added to the topical composition, as long as they are pharmaceutically acceptable and not deleterious to the epithelial cells or their function. Further, they should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like may be present. The pH of the topical composition of this invention may be adjusted to a physiologically acceptable range of from about 6.0 to about 9.0 by adding buffering agents thereto in order for the composition to be physiologically compatible with the skin Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer' solution, or physiologically buffered saline. Aqueous injection suspensions may contain substances which increase the viscosity of the suspension, such as sodium carboxymethyl cellulose, sorbitol, or dextran. Additionally, suspensions of the active solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For nasal administration, penetrants appropriate to the particular barrier to be permeated are used in the formulation. Such penetrants are generally known in the art.

The pharmaceutical compositions of the present invention may be manufactured in a manner known in the art, e.g. by means of conventional mixing, dissolving, granulating, dragee-making, levitating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder, optionally including additives such as 1 mM-50 mM histidine, 0.1%-2% sucrose, 2%-7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition with information including amount, frequency and method of administration.

The invention also includes the use of a compound such as an FLT3 inhibitor, a phosphatase (PP2A or PP1) inhibitor, a p38 MAP kinase inhibitor, a TGF-beta receptor inhibitor, c-kit inhibitor, src inhibitor, RNA-dependent protein kinase inhibitor, or any compound disclosed herein (or a salt thereof) in the manufacture of a medicament for neuroprotection.

Combination Therapy

In certain embodiments, the invention contemplates combination therapies. For example, compound of the invention (which may be an flt3 inhibitor such) can be used in therapy in combination with other compounds. For example, a compound of the invention can be co-administered in combination with other compounds, for example, at a ratio in the range of 1:1-1:5-5:1, 1:1-1:10-10:1, 1:1-1:25-25:1, 1:1-1:100-100:1, 1:1-1:1000-1000:1 or 1:1-1:10,000-10,000:1. For example, in the treatment of glaucoma, other anti-glaucoma medicaments can be used, such as: beta-blockers, including levobunolol (Betagan), timolol (Betimol, Timoptic), betaxolol (Betoptic) and metipranolol (OptiPranolol); alpha-agonists such as apraclonidine (Iopidine) and brimonidine (Alphagan); carbonic anhydrase inhibitors, such as acetazolamide, methazolamide, dorzolamide (Trusopt) and brinzolamide (Azopt); prostaglandins or prostaglandin analogs such as latanoprost (Xalatan), bimatoprost (Lumigan) and travoprost (Travatan); miotic or cholinergic agents, such as pilocarpine (Isopto Carpine, Pilopine) and carbachol (Isopto Carbachol); epinephrine compounds, such as dipivefrin (Propine); forskolin; or neuroprotective compounds such as brimonidine and memantine. In certain embodiments, the compound used in combination with the compound of the invention is not an anti-angiogenic agent such as a steroid derivative such as 2-methoxyestradiol or analogs or derivatives thereof.

Other combination therapies contemplated by the invention includes treatment with a compound of the invention in combination with surgery, e.g., surgical relief of intraocular pressure, e.g., via trabeculectomy, laser trabeculoplasty, or drainage implants.

Dosage and Mode of Administration

As described, these compounds may be administered to humans and other animals for therapy by any suitable route of administration, including orally, nasally, or ocularly, as by, for example, a spray, rectally, intravaginally, parenterally, intracisternally and topically, as by powders, ointments or drops (including eyedrops), including buccally and sublingually. For example, for ocular administration, an eyedrop formulation can include an effective concentration of a compound of the invention together with other components such as buffers, wetting agents and the like. Intravitreal injection may also be employed to administer a compound to the eye.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, doses of the compounds of this invention for a patient will range from about 0.0001 to about 1000 mg per kilogram of body weight per day. In certain embodiments, the dosage is between about 1 µg/kg and about 500 mg/kg, more preferably between about 0.01 mg/kg and about 50 mg/kg. For example, in certain embodiments, a dose can be 1, 5, 10, 15, 20, or 40 mg/kg/day.

If desired, the effective daily dose of the active compound may be administered as two, three, four, five, six or more sub-doses administered separately at appropriate intervals throughout the day, optionally, in unit dosage forms.

The patient receiving this treatment is any animal in need, including primates, in particular humans, and other mammals such as equines, cattle, swine and sheep; and poultry and pets in general. An animal in need, in preferred embodiments, is a subject suffering from or susceptible to a neurodegenerative disease or disorder such as glaucoma, e.g., a subject diagnosed as suffering from or susceptible to a neurodegenerative disease or disorder.

The compound of the invention can be administered as such or in admixtures with pharmaceutically acceptable and/or sterile carriers and can also be administered in conjunction with other agents such as antibiotics, neuroprotectants, and other therapeutic agents. Conjunctive therapy thus includes sequential, simultaneous and separate administration of the active compound in a way that the therapeutic effects of the first administered one is not entirely disappeared when the subsequent is administered.

The dosage range for administration will be adjusted by the physician as necessary.

Therapeutic Methods

Preferred compounds and amounts for use in the therapeutic methods of the invention produce at least about 10% to 15% decrease in cell loss or loss of function relative to cell survival or cell function measured in absence of the tested compound in an assay, more preferably at least about a 20% or 25% decrease relative to a control, and still more preferably induce at least about 20%, 30%, 40%, 50%, 60%, 70%, 80%, 90% or 100% decrease in cell loss or loss of function relative to absence of the tested compound in such an assay. In other embodiments, the preferred compounds and amounts for use in the therapeutic methods of the invention produce at least about 10% to 15% increase in neuron count, neuron function, neurite count, neurite total length, or neurite average length relative to absence of the tested compound in an assay.

The methods of the invention can be used to treat any neurodegenerative disease or disorder (including traumatic injury) in which neuronal cell loss is implicated, or in which damage to neurites is involved. Thus, for example, the methods of the invention can be used to treat neurodegenerative disorders such as or associated with alcoholism, Alexander's disease, Alper's disease, Alzheimer's disease, amyotrophic lateral sclerosis (Lou Gehrig's Disease), ataxia telangiectasia, Batten disease (also known as Spielmeyer-Vogt-Sjogren-Batten disease), bovine spongiform encephalopathy (BSE), Canavan disease, Cockayne syndrome, corticobasal degeneration, Creutzfeldt-Jakob disease, frontotemporal lobar degeneration, Huntington's disease, HIV-associated dementia, Kennedy's disease, Krabbe's disease, Lewy body dementia, neuroborreliosis, Machado-Joseph disease (Spinocerebellar ataxia type 3), Multiple System Atrophy, multiple sclerosis, Niemann Pick disease, Parkinson's disease, Pelizaeus-Merzbacher Disease, Pick's disease, primary lateral sclerosis, prion diseases, Progressive Supranuclear Palsy, Refsum's disease, Sandhoffs disease, Schilder's disease, subacute combined degeneration of spinal cord secondary to pernicious anemia, Spielmeyer-Vogt-Sjogren-Batten disease (also known as Batten disease), spinocerebellar ataxia (multiple types with varying characteristics), spinal muscular atrophy, Steele-Richardson-Olszewski disease, and tabes dorsalis. In addition, methods of the invention can be used to treat neuronal damage due to traumatic injury or stroke (e.g., by preventing death of damaged neuronal cells and/or by promoting or stimulating neurite growth from damaged neuronal cells).

In certain embodiments, the method can be used to treat glaucoma, including primary open angle glaucoma (POAG), and angle closure glaucoma, as well as normal tension glaucoma and secondary glaucomas. In certain embodiments, the glaucoma is not neovascular glaucoma.

In certain embodiments, the subject has been identified (e.g., diagnosed) as suffering from or susceptible to a neurodegenerative disease or disorder (including traumatic injury) in which neuronal cell loss is implicated, or in which damage to neurites is involved, and for which treatment or prophylaxis is desired. In certain embodiments, the subject is not suffering, or has not been diagnosed as suffering, from cancer. In certain embodiments, the subject is not suffering, or has not been diagnosed as suffering, from a disorder related to excess angiogenesis. In certain embodiments in which a cell is contacted with a compound of the invention, or a pharmaceutically acceptable salt, the cell is not a neoplastic cell. In certain embodiments of the above aspects, the cell is a mammalian cell, more preferably a human cell.

In certain embodiments, the present methods are applicable to cell culture techniques wherein it is desirable to prevent neuronal cell death or loss of neuronal function. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). One use of certain embodiments of the present methods is in cultures of neuronal cells, such as in the use of such cultures for the generation of new neurons and glia. In such embodiments of the subject methods, the cultured cells can be contacted with a compound of the present invention in order to prevent neuronal cell death or loss of neuronal function. In an exemplary embodiment, the subject method can be used to culture, for example, sensory neurons or, alternatively, motoneurons. Such neuronal cultures can be used as convenient assay systems as well as sources of implantable cells for therapeutic treatments.

In certain embodiments, the methods of the invention can be used to improve the survival or integration of transplanted neuronal cells into a host subject. Thus, for example, a subject receiving a transplant of neuronal cells can be treated (before, during, or after the transplantation procedure) with compounds according to the methods of the present invention, to prevent cell death of the transplanted cells (or host cells that may be perturbed during the transplantation procedure), and/or to promote the growth of neurites in the transplanted cells or the host neuronal cells, and thereby promote integration of the transplanted cells into the host nervous system.

Kits or Pharmaceutical Systems

The present compounds and compositions may be assembled into kits or pharmaceutical systems for use in treatment of neurodegenerative diseases, disorders, or conditions. Kits or pharmaceutical systems according to this aspect of the invention include a compound as described herein, preferably in unit dosage form. The compound may be present together with a pharmaceutically acceptable solvent, carrier, excipient, or the like, as described herein.

The kits or pharmaceutical systems of the invention may also include associated instructions for using the compounds of the invention for treating a neurodegenerative disease or disorder. The instructions will generally include information about the use of the compound for treatment of a disease or disorder or symptoms thereof; in preferred embodiments, the instructions include at least one of the following: description of the active compound; dosage schedule and administration for treatment of a neurodegenerative disease or disorder; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The kit may also include one or more container means, such as vials, tubes, ampules, bottles and the like, for containing the compound (and optionally carried within a carrier means, such as a box, carton, tube or the like). Such containers can be made of plastic, glass, laminated paper, metal foil, or other materials suitable for holding medicaments.

EXAMPLES

Preparation of Synthetic Precursors

Certain reagents are commercially available or can be prepared using no more than routine experimentation by one of ordinary skill in the art based on known procedures. Certain synthetic precursors were prepared as described herein.

5-mercaptooxindole

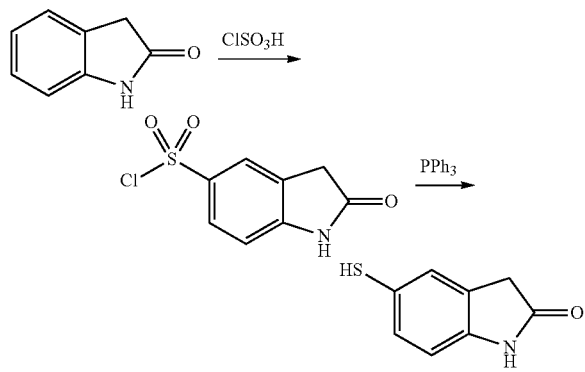

Chlorosulfonic acid 115 mL (1.73 mol) in a 1 L widemouth round flask (with a 45/50 joint, equipped with a gas outlet tube) was cooled on ice bath and solid oxindole 25.60 g (192.2 mmol) was gradually spooned in with vigorous stirring and cooling on ice, over a 20 min period. After the complete addition, the flask was removed from the cooling bath and the mixture was stirred for additional 15 min. The flask was then placed on a 70° C. oil bath and the mixture was stirred at 70° C. for 2 hours. The resulting dark reaction mix was cooled on ice, then very cautiously poured in a thin stream onto crushed ice 1.4 kg that was pre-chilled in a freezer, in a 3 L beaker, with stirring. The quenched mixture was stirred until all ice melted, the precipitated solid was collected by filtration on a very large glass Buchner funnel, washed with 0.05 M HCl, semi-dried by filtration and then thoroughly dried under high vacuum ("highvac") over a 60 hour period. Y=42.23 g (95% th) of a tan solid.

The 5-chlorosulfonyl oxindole from the previous step, 42.23 g (182.3 mmol) was suspended in anhydrous dichloromethane (100 mL) in a 1 L round flask. The mixture was cooled on ice slush bath and a solution of triphenylphosphine 167.5 g (638 mmol, 3.5 eq.) in anhydrous dichloromethane (300 mL) was dropwise added from an addition funnel under nitrogen with cooling over a 45 min period. After complete addition the flask was removed from the cooling bath and the mixture was stirred at room temperature for 3 hours. The reaction was quenched by water addition, 200 mL. The flask with the biphasic mixture was placed on a 50° C. water bath and the mixture was refluxed under nitrogen for 1 hour, then cooled on ice. The precipitated product was collected by filtration, washed thoroughly with ice-chilled dichloromethane and ice water, then dried by suction and on highvac, to provide 19.58 g of a pure product. The biphasic filtrates were de-oxygenated by argon/vacuum purge (3 times). The mixture was made strongly alkaline by addition of 50% aq. NaOH solution, shaken under Ar and then rapidly separated. The organic phase was re-extracted with water. The aqueous phases were promptly washed with fresh dichloromethane (200 mL). The combined aqueous extracts were made acidic by addition of 6M HCl, the mixture was cooled on ice, the precipitated product was collected by filtration, washed with ice-cold water, dried by suction and on highvac, to provide a second crop of the product, 7.15 g. The combined yield was 26.73 g (88.5% th) of a light tan solid. 1H-NMR ($d_6$-DMSO, 400 MHz): 10.339 (s, 1H), 7.151 (s, 1H), 7.108 (m, 1H), 6.707 (d, 8.0 Hz, 1H), 5.109 (s, 1H), 3.436 (s, 2H)

5-methylsulfoxyoxindole

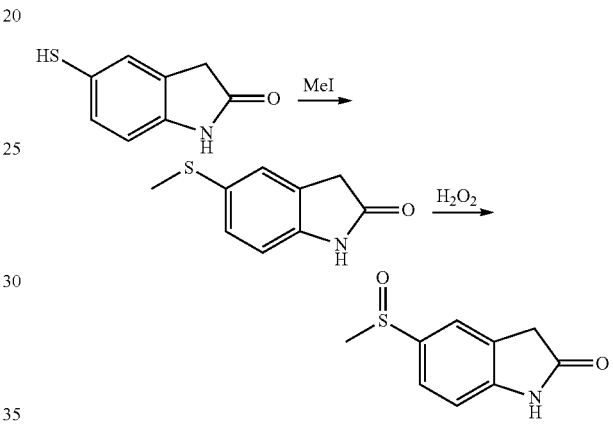

5-mercaptooxindole 26.73 g (161.8 mmol) and $K_2HPO_4$ 45 g (258 mmol) was suspended in methanol 420 mL. The mixture was diluted with water 210 mL and methyl iodide 14.0 mL (225 mmol) was added. The mixture was vigorously stirred under reflux condenser on a 50° C. bath for 1 hour. The reaction mixture was cooled to ambient temperature, the solution was decanted from the solids and the solution was concentrated to a small volume on rotary evaporator ("rotovap"). The decanted solids were dissolved in water (o.6 L) and combined with the concentrated solution. The mixture was stirred for 15 minutes, the precipitate was collected by filtration, dried by suction and on highvac. The obtained crude intermediate (22.84 g) was dissolved in toluene 0.9 L at reflux, the resulting cloudy solution was filtered while hot. The filtrates were concentrated to a small volume and then diluted with excess of hexanes (0.5 L). The precipitated 5-methylthiooxindole was collected by filtration, washed with hexanes and dried. Y=21.78 g (75%) of a light tan solid.

5-methylthiooxindole from the previous step, 2.05 g (11.44 mmol) was dissolved in 98% formic acid 31 mL and acetic acid 5 mL was added. The solution was cooled to 0° C. and 35% hydrogen peroxide 1.0 mL (11.42 mmol) was gradually injected into the stirred reaction mixture over a 10 min period. The reaction was kept on an ice bath for an additional 1 hour, then evaporated to dryness. The obtained semi-crystalline residue was suspended in ethyl acetate 10 mL with sonication (10 min), the precipitated product was collected by filtration, washed with a small volume of ethyl acetate and dried. Concentrating the filtrates provided an additional second crop of the product. The combined yield was 2.067 g (92.5%) of a pure methyl sulfoxide product as a pink-white powder.

5-ethylsulfoxyoxindole

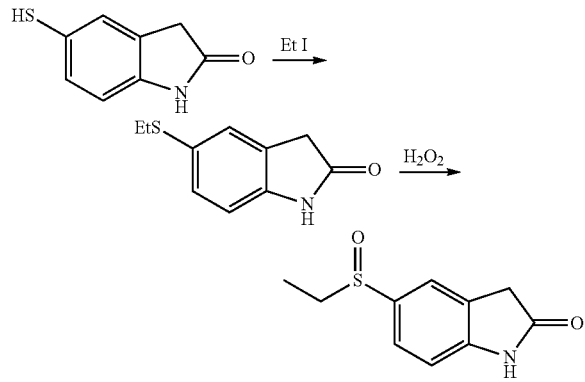

Under reaction conditions analogous to the preparation of 5-methylsulfoxyoxindole, alkylation of 5-mercaptooxindole 1.99 g (12.05 mmol) with ethyl iodide 1.35 mL (16.7 mmol) in aqueous methanol at 50° C. in the presence of hydrogen phosphate provided 2.152 g of 5-ethylthiooxindole (92.5%).

5-ethylthiooxindole 1.200 g (6.21 mmol) was oxidized with one equivalent of hydrogen peroxide (0.38 mL of 50% $H_2O_2$) in formic-acetic acid mixture at 0° C. to provide a crude material which was purified on a column of silica (40 g), by using a gradient of ethyl acetate in dichloromethane linear gradient, followed by 5% methanol in ethyl acetate, to provide 1.178 g (90.5%) of a pure ethylsulfoxide product as a white hygroscopic solid.

4-methyl-5-methylsulfoxyoxindole

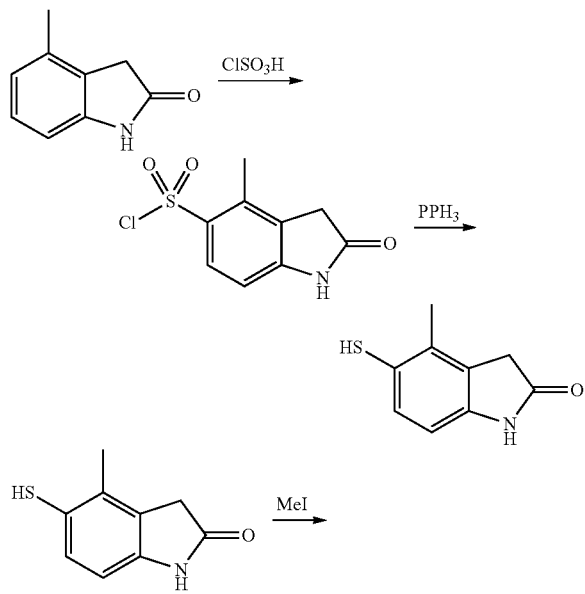

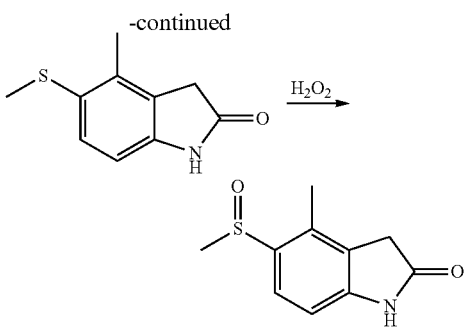

Under reaction conditions analogous to preparation of 5-mercaptooxindole, chlorosulfonylation of 4-methyloxindole 3.15 g (21.40 mmol) with neat chlorosulfonic acid 25 mL provided 4.55 g of 5-chlorosulfonyl-4-methyloxindole (86.5% Y, 95% isomeric purity by $^1$H-NMR, in d6-acetone) which was reduced with triphenyl phosphine 17.0 g (65 mmol) in anhydrous dichloromethane, to provide a crude thiol 2.573 g (75% Y) which was then methylated with excess of methyl iodide (1.50 mL; 24 mmol) to provide a crude methylthio intermediate 2.722 g (98% Y, 90% pure), by using conditions analogous to preparation of 5-methylsulfoxyoxindole.

The crude 4-methyl-5-methylthio oxindole intermediate 1.008 g (5.215 mmol) was dissolved in a mixture of 98% formic acid 30 mL and acetic acid 10 mL. The solution was cooled to 0° C., 50% hydrogen peroxide 0.29 mL (4.731 mmol) was added over 10 minutes, the cooling bath was then removed and the reaction was stirred at ambient temperature for 3 hours. The reaction mixture was diluted with water 150 mL, two spoons of activated charcoal were added, the mixture was stirred for 10 minutes and filtered (the charcoal was washed with water). The combined filtrates were evaporated on a rotovap and the residue was dried on highvac. The obtained sticky residue was suspended in acetonitrile 20 mL, the precipitated solids were collected by filtration, washed with acetonitrile and dried. Concentrating the supernatants yielded a second crop of the sulfoxide product. The combined yield was 805 mg (73.5%) of a white solid. 1H-NMR (d$_6$-DMSO, 400 MHz): 10.60 (br s, 1H), 7.62 (d, 8.1 Hz, 1H), 6.90 (d, 8.1 Hz, 1H), 3.52 (d$_{AB}$, 22.3 Hz, 1H), 3.44 (d$_{AB}$, 22.3 Hz, 1H), 2.63 (s, 3H), 2.22 (s, 3H)

Oxindole-5-carboxylic acid

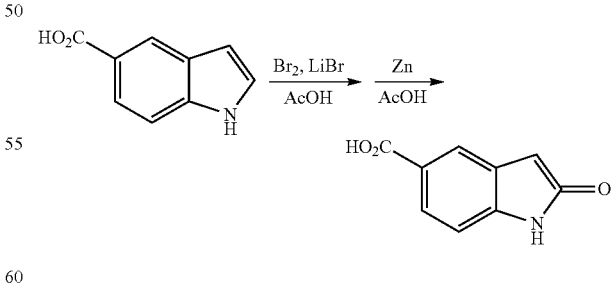

Indole-5-carboxylic acid 5.00 g (31.0 mmol) solution in ethanol 99% 120 mL and tert-butanol 180 mL in a 1 L RB flask was cooled on ice bath to +5° C. Meanwhile, a solution of lithium bromide 9.0 g (103.6 mmol) in neat acetic acid 60 mL was placed into an addition funnel Neat bromine 5.0 mL (16.0 g; 100.1 mmol) was then charged to this LiBr solution and the resulting bromine+LiBr solution was dropwise added into the vigorously stirred indolecarboxylic acid solution at +5° C. over a 90 min period. (After a complete addition the addition funnel was then washed with EtOH (2×5 mL) and the washings were added to the reaction mix). At the end of the bromine addition the cooling bath was let to expire and the reaction mix was stirred at +5 to +15° C. bath for 1 hour and at 15° C. for additional 15 min. The reaction mixture was then diluted with additional acetic acid 100 mL. Zn dust 20 g [Aldrich; <10 μM] (306 mmol) was added in one portion (gas evolution) and the mixture was stirred in an open flask on ambient water bath overnight (16 hours). The next day, the precipitated solids were collected by filtration, washed with ethanol and dried by suction. The solid (containing a mix of the product, unreacted Zn metal and Zn salts) was transferred into a large beaker on a hotplate, suspended in boiling methanol (300 mL) and filtered. The extraction with boiling methanol was repeated twice more, to separate the unreacted Zn metal from the product. The combined methanolic filtrates were evaporated to dryness. Separately, the acetic acid+LiBr—containing filtrates from the reaction mix were concentrated to a small volume on rotovap and the produced salt-rich residue was diluted with water 0.6 L and acidified with 6M HCl to about pH=1.5. This mixture was then combined with the evaporation residue obtained from the methanolic filtrates. The solids in the flask were re-suspended by a brief sonication (5 min) and the slurry was cooled down on ice bath, then placed into a freezer (−20° C.) for 4 hours. The precipitated product was collected by filtration, washed with ice-cold water, dried by suction and on highvac. Y=5.23 g (95%) of a light tan solid. 1H-NMR (d6-DMSO, 400 MHz): 12.58 (br s, 1H), 10.72 (s, 1H), 7.82 (dd, 8.3 Hz, 1.6 Hz, 1H), 7.75 (s, 1H), 6.88 (d, 8.3 Hz, 1H), 3.54 (s, 2H)

Oxindole-5-carboxylic acid amides—A General Procedure

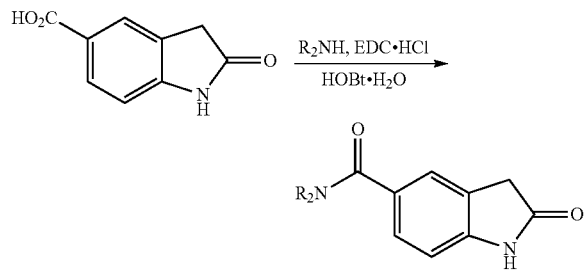

A suspension of oxindole-5-carboxylic acid 1.90 g (10.72 mmol) and HOBt·H₂O 1.90 g in chloroform 40 mL was treated with EDC.HCl 2.90 g and 2 equivalents of secondary amine (21 mmol). The mixture was stirred for 1-2 days, at which point the mixture became pink and nearly homogeneous, and HPLC indicated a complete conversion of the starting material. The reaction mixture was applied onto a column of silica 60 g (in chloroform) that was layered over with activated basic alumina (about 15 g). The column was eluted with methanol gradient in chloroform, 0 to 6% MeOH. The column-purified material was finally re-crystallized from a suitable solvent. The typical product yield was 45-90% of theory.

In the case of dimethylamine, the procedure was modified: dimethylamine was added as 40% aqueous solution and the used solvent was DMF. The reaction mixture was evaporated and dried on higvac before the chromatographic purification. The column-purified product was re-crystallized from a small volume of ethyl acetate.

4-ethoxycarbonyl-3,5-dimethylpyrrole-2-carboxylic acid tBu ester

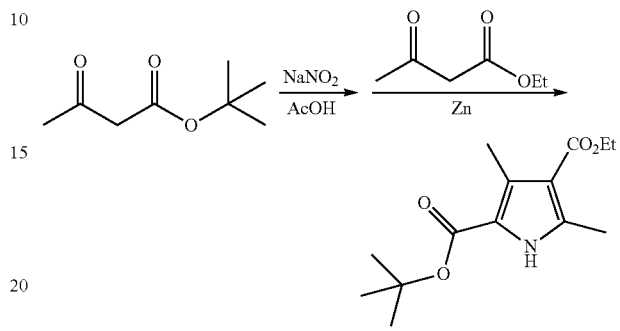

A solution of tert-butyl acetoacetate 31.65 g (200 mmol) in acetic acid 40 mL was cooled on ice bath to 5° C. and a solution of NaNO2 14.00 g (1 eq.) in water 20 mL was injected slowly into the reaction mix with cooling and vigorous stirring, over a 20 min period, so that the internal temperature did not exceed +15° C. The syringe was washed with water (2×3 mL) and the washings also added to the mix. The reaction mix was stirred on melting ice bath to RT in an open flask overnight (16 hours). Separately, in a 3-necked 1 L round bottom flask with a large egg-shaped stirbar and internal thermometer and an addition funnel, anhydrous sodium acetate 20 g and ethyl acetoacetate 29.0 g (1.1 eq.) were dissolved in acetic acid 100 mL on a 60° C. oil bath. With vigorous stirring, Zn dust 10 g (Aldrich, <10 μm) was then added followed by dropwise addition of the nitrosated mixture (from tBu acetoacetate and sodium nitrite). This addition was carried out over a 45 min period, while an additional Zn dust 40 g was simultaneously added to the mix in approx 5 g portions few minutes apart. Each Zn addition was accompanied by a temperature spike, the internal temperature in the flask was kept below +85° C. (The bath temperature was 60° C. and the internal temperature in the flask was controlled by the rate of addition of Zn dust and the nitrosation mix. The total quantity of used Zn dust was 50 g). At the end, the addition funnel was washed with additional acetic acid (3×10 mL) and this was added to the mix and continued for 1 more hour at 60 C. The resulting foamy reaction mixture was finally diluted by addition of water, 100 mL, and the mixture was stirred for one more hour at 60 C. The reaction mix was then poured into a large beaker, diluted with water 0.5 L, some crushed ice was added (total mix volume was 1.5 L) and the slurry was placed on ice bath and stirred for 1 hour. The precipitate was collected by filtration, washed thoroughly with water and dried by suction. The obtained crude product was dissolved in a 1:1 mix of ethanol+ethyl acetate (0.5 L) with gentle heating, the solution was filtered from the leftover Zn dust (Zn washed with EtOAc on Buchner) and the filtrates were evaporated to dryness. The solid residue was suspended in acetonitrile 60 mL and the slurry was placed into a freezer (−20° C.) overnight. The precipitate was collected by filtration, washed with cold acetonitrile, dried by suction and on highvac. Y=35.55 g (66.5%) of a white sugar-like crystalline solid. 1H-NMR (CDCl$_3$, 400 MHz): 8.93 (br s, 1H), 4.29 (q, 7.1 Hz, 2H), 2.53 (s, 3H), 2.50 (s, 3H), 1.57 (s, 9H), 1.36 (t, 7.1 Hz, 3H)

2-formyl-3,5-dimethylpyrrole-4-carboxylic acid

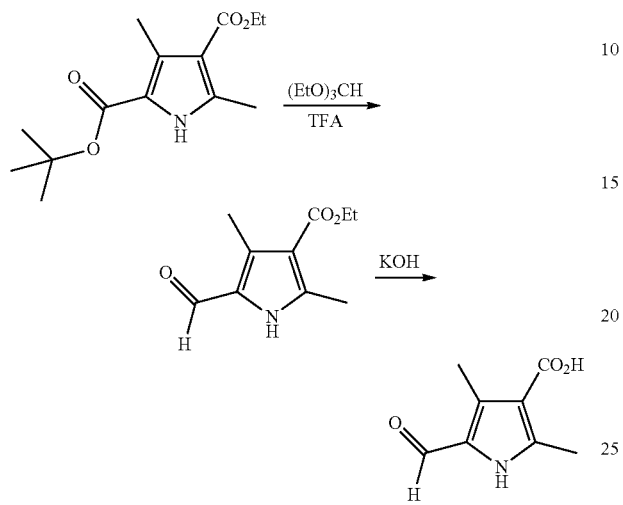

4-ethoxycarbonyl-3,5-dimethylpyrrole-2-carboxylic acid tert-Bu-ester 16.35 g was dissolved in neat trifluoroacetic acid 85 mL and the solution was stirred at room temperature for 30 min (the mix turned Burgundy red with gas evolution), then cooled to +5° C. on ice/water bath. Neat triethyl orthoformate 16.5 mL (1.6 eq.) was added and the mix was stirred at +5° C. for 35 min, then concentrated on rotovap from ambient water bath to a small volume. The residue was diluted gradually with water addition, 300 mL, the resulting slurry was shaken for 5 min and the precipitated ethyl ester intermediate was collected by filtration, washed thoroughly with water and dried by suction.

This ethyl ester intermediate was suspended in ethanol 150 mL, placed on a 120° C. oil bath and stirred to complete dissolution. A solution of KOH 20 g (pellets, 85%) in water 200 mL was then added to the mix, the flask was equipped with a short-path distillation adaptor and the reaction mixture was distilled under a stream of nitrogen gas on a 120° C. oil bath for 90 min. (Only water distilled at this point and the ethyl ester hydrolysis was complete by HPLC). The reaction mixture was cooled, charcoal (5 spoons) was added and the reaction mix was then stirred on ambient water bath for 30 min, and filtered (the charcoal was thoroughly washed with water). The combined filtrates were acidified with addition of 6M HCl, the precipitated product was collected by filtration on a large Buchner funnel, washed with water and semi-dried by suction. The crude product was dissolved in EtOH (900 mL) at reflux, the solution was allowed to crystallize at ambient temperature overnight (14 hours). The product was collected by filtration, washed with EtOH, dried by suction and on highvac. Concentrating the supernatants to a small volume, diluting the slurry with ethanol 100 mL and refluxing the mix for 30 min, then letting the mix to crystallize at RT overnight provided a second crop of a pure product. The combined yield was 8.32 g (81% overall) of a light-tan crystalline solid. 1H-NMR (d$_6$-DMSO, 400 MHz): 12.12 (s, 1H), 12.10 (very br s, 1H), 9.61 (s, 1H), 2.46 (s, 3H), 2.42 (s, 3H)

3,5,5-trimethyl-4-oxo-4,5,6,7-tetrahydroindole

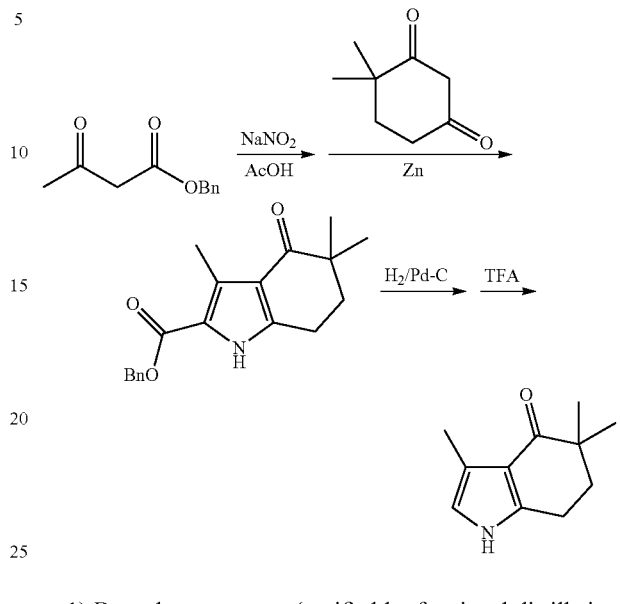

1) Benzyl acetoacetate (purified by fractional distillation on highvac) 38.5 g (200 mmol) was dissolved in acetic acid 63 mL and the mixture was cooled on ice bath and stirred until a precipitate of solid acetic acid begun to form. Then a solution of sodium nitrite 22.0 g (319 mmol) in water 62 mL was added dropwise over a 30 minute period so that the reaction temperature remained below +15° C. The cooling bath was then allowed to expire and the mixture was stirred at amibient temperature for additional 5 hours. The reaction mixture was then partitioned between ether 200 mL and water, the organic extract was separated, washed with water, then gradually basified by addition of saturated aqueous sodium bicarbonate 200 mL, separated and finally washed with half-saturated brine. The aqueous phases were re-extracted with ether. Combined organic extracts were dried (Na$_2$SO$_4$) and evaporated, the residue was dried on highvac. Y=39.32 g (89%) of benzyl acetoacetate-2-oxime (E/Z mixture) as a pale yellow honey. The material was used as a 20% wt solution in acetic acid for the following step.

2) 4,4-Dimethyl-1,3-cyclohexanedione 5.04 g (35.95 mmol) and anhydrous sodium acetate 5.0 g was dissolved in acetic acid 50 mL on a 75° C. oil bath in an open flask. A 20% solution of benzyl acetoacetate-2-oxime in acetic acid 43.75 g (1.1 eq.) was added dropwise over 20 minutes at 75° C. together with Zn dust 15.0 g (Zn dust was added in five portions, approximately 3 g each, several minutes apart). The oil bath temperature was then raised to 100° C. and the mixture was stirred at 100° C. for 3 hours. The reaction mixture was cooled, poured into cold water 0.7 L and sludge was stirred for one day. The solidified crude product was collected by filtration, washed thoroughly with water and dried. The crude material was dissolved in ethyl acetate 250 mL, filtered and the filtrate was concentrated to a small volume. The evaporation residue was gradually diluted with cyclohexane 100 mL and the solution was inoculated mechanically, then allowed to crystallize for 1 hour. The precipitated product was collected by filtration and re-crystallized once more from a mixture of benzene 20 mL and cyclohexane 100 mL. Y=4.613 g (41%) of 3,5,5-trimethyl-4-oxo-4,5,6,7-tetrahydroindole-2-carboxylic acid benzyl ester. 1H-NMR (d6-DMSO, 400 MHz): 11.93 (br s, 1H), 7.40 (m, 5H), 5.30 (s, 2H), 2.77 (t, 6.3 Hz, 2H), 2.48 (s, 3H), 1.86 (t, 6.3 Hz, 2H), 1.05 (s, 6H); 13C-NMR (d6-DMSO, 100 MHz): 199.06, 160.62, 145.21, 136.44, 128.45 (2C), 128.09, 127.95, 127.81 (2C), 118.92, 117.28, 65.01, 41.65, 36.34, 24.24, 19.34, 11.37

3) 3,5,5-trimethyl-4-oxo-4,5,6,7-tetrahydroindole-2-carboxylic acid benzyl ester from the previous step, 6.60 g (21.20 mmol) and 2.0 g of 10% Pd—C was suspended in ethyl acetate 150 mL and hydrogenated under balloon of hydrogen for 3 hours. The reaction mixture was diluted with methanol 0.5 L and the mixture was stirred under Ar for 30 min to dissolve the precipitated carboxylic acid intermediate. The catalyst was then removed by filtration and the filtrates were evaporated to dryness and dried on highvac. The residue was dissolved in trifluoroacetic acid 40 mL, the solution was stirred on a 45° C. bath for 30 min, then evaporated to dryness. The residue was dried on highvac. The crude material was applied onto a column of silica (60 g) in dichloromethane and eluted with 10:1 dichloromethane-ethyl acetate mixture. Y=3.17 g (84% overall) of 3,5,5-trimethyl-4-oxo-4,5,6,7-tetrahydroindole as a white solid that gradually turns pink on air and light. 1H-NMR (d6-DMSO, 400 MHz): 10.89 (br s, 1H), 6.44 (s, 1H), 2.72 (t, 6.3 Hz, 2H), 2.12 (s, 3H), 1.85 (t, 6.3 Hz, 2H), 1.04 (s, 6H)

3,5,5-trimethyl-4-oxo-4,5,6,7-tetrahydroindole-2-carboxaldehyde

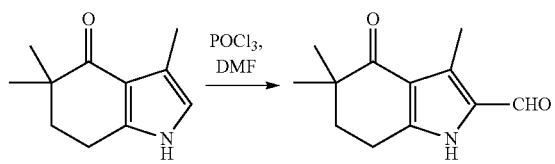

POCl₃ 1.2 mL (13.1 mmol) was added dropwise into anhydrous DMF 15 mL with cooling on ice bath. After 10 minutes, a solution of 3,5,5-trimethyl-4-oxo-4,5,6,7-tetrahydroindole 1.500 g (8.463 mmol) in anh. DMF was added dropwise over a 10 min period. The cooling bath was allowed to expire and the reaction was stirred at ambient temperature overnight (11 hours). With cooling on ice bath, the reaction mixture was quenched by addition of crushed ice and ice-cold water (approx 150 mL total). The reaction mixture was then alkalized to pH=10 (approximately, on pH paper strip) by gradual addition of potassium carbonate solution, the total volume was adjusted to about 250 mL with additional water and the mixture was stirred at ambient temperature for 1 day. The resulting slurry was cooled on ice bath, the precipitated product was collected by filtration, washed with ice-cold water, dried by suction and on highvac. Y=1.351 g (77.5%) of a white microcrystalline solid. 1H-NMR (d6-DMSO, 400 MHz): 12.14 (br s, 1H), 89.66 (s, 1H), 2.79 (t, 6.1 Hz, 2H), 2.48 (s, 3H), 1.86 (t, 6.3 Hz, 2H), 1.06 (s, 6H)

4,5,6,7-tetrahydroindole-2-carboxaldehyde

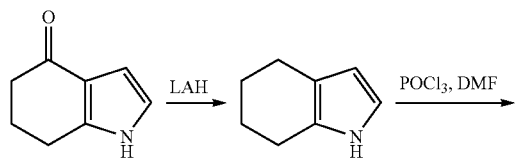

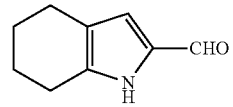

4-oxo-4,5,6,7-tetrahydroindole 5.15 g (38.1 mmol) was gradually added to a stirred slurry of lithium aluminum hydride 4.0 g in anhydrous THF 0.45 L with cooling on ambient water bath, portion-wise, over 30 min period. The mixture was then placed on oil bath and refluxed under Ar on a 75-80° C. oil bath for 26 hours. The reaction mixture was cooled on ambient water bath, quenched by sequential addition of ethyl acetate 4 mL followed by dropwise water addition, 4 mL (very slowly, gas evolution), followed by 15% wt NaOH solution 12 mL followed by additional water 4 mL. The resulting slurry was stirred vigorously for 30 min, the salts were removed by filtration (the cake was washed thoroughly with THF) and the filtrates were concentrated on a rotovap. The oily residue was distilled on highvac using a short-path distillation apparatus, to provide 3.83 g (84%) of tetrahydroindole as oily liquid that turns yellow on light and air exposure, by 57-60° C./0.7 Torr.

Anhydrous DMF 20 mL in a 250 mL flask was cooled on ice bath and neat POCl₃ 4.6 mL (50 mmol) was added dropwise under Ar. After 10 min, a solution of tetrahydroindole 3.83 g (32.14 mmol) in anh DMF 10 mL was gradually added over 10 min (exothermic) followed by additional anh DMF 2×5 mL to wash the flask and the syringe. The cooling bath was replaced with ambient water bath and the reaction was stirred at RT under Ar for 13 hours (overnight). The reaction was quenched by addition of water 20 mL followed by 15% wt NaOH solution 40 mL. After 10 min, additional 15% NaOH 25 mL was added, followed by water 100 mL and the mixture was stirred vigorously for 30 min on ambient water bath. The precipitated product was collected by filtration, compressed on the Buchner funnel, washed thoroughly with water, dried by suction and on highvac. Y=4.282 g (90.5%) of light tan shiny flakes. 1H-NMR (d₆-DMSO, 400 MHz): 11.609 (br s, 1H), 9.268 (s, 1H), 6.679 (s, ¹H), 2.557 (t, 5.9 Hz, 2H), 2.446 (t, 5.9 Hz, 2H), 1.693 (m, 4H) 2,5,5-trimethyl-4,5,6,7-tetrahydroindole-2-carboxaldehyde

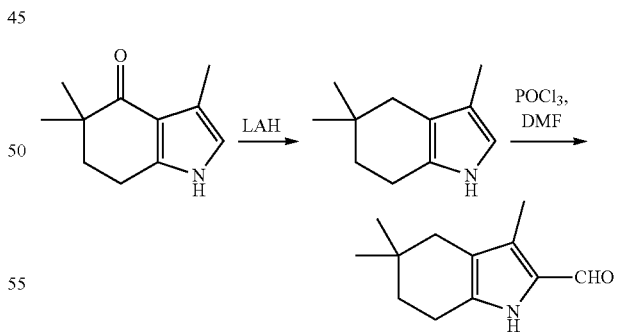

Using a procedure closely analogous to the preparation of 4,5,6,7-tetrahydroindole-2-carboxaldehyde, 3,5,5-trimethyl-4-oxo-4,5,6,7-tetrahydroindole 1.65 g (9.31 mmol) was reduced by 36-hour reflux with lithium aluminum hydride 2.0 g in anh. THF (100 mL) to provide 1.50 g (98%) of 2,5,5-trimethyl-4,5,6,7-tetrahydroindole (light tan crystalline solid) that was formylated with a mixture of anhydrous DMF 20 mL and POCl₃ 1.5 mL to provide the title aldehyde product 1.669 g (93% overall) as a tan solid. 1H-NMR (d6-DMSO, 400 MHz): 11.31 (br s, 1H), 9.43 (s, 1H), 2.51 (m, 2H), 2.14 (s, 3H), 2.13 (s, 2H), 1.49 (t, 6.6 Hz, 2H), 0.94 (s, 6H)

6,6-dimethyl-4-oxo-4,5,6,7-tetrahydroindole-2-carboxaldehyde

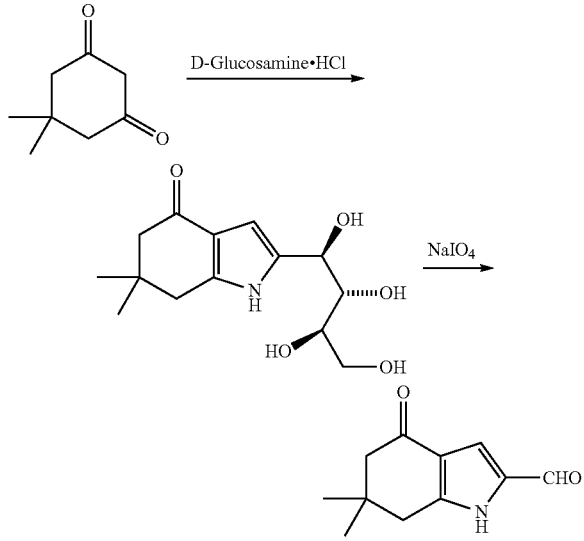

Dimedone 4.80 g (34.24 mmol) and D-glucosamine.HCl 6.67 g (30.9 mmol) were combined in water 20 mL. Acetone 30 mL was added, followed by solid $Na_2CO_3$ 1.643 g (15.5 mmol) and additional water 20 mL. The mixture was stirred in a closed flask for 11 days. The reaction mixture was concentrated on rotovap from ambient waster bath to half volume, the precipitated tetraol intermediate was collected by filtration, washed with ice-cold water and chloroform, then dried, to provide 3.189 g of the intermediate as a yellow-white powder. Additional crop (330 mg) was obtained by concentrating the filtrates to dryness and re-crystallizing the residue from water (20 mL, +5° C. overnight). The combined two crops of the intermediate, 3.520 g (12.42 mmol) were suspended in water 100 mL and the slurry was cooled to 0° C. Ice-cold solution of sodium periodate 10.70 g (50 mmol) in water 100 mL was gradually added over a 10 min period. The mixture was vigorously stirred on ice bath for 1 hour. The precipitated product was collected by filtration, washed with ice-cold water and dried. Y=2.159 g of a pale yellow solid (36.5% overall). 1H-NMR (d6-DMSO, 400 MHz): 12.51 (br s, 1H), 9.50 (s, 1H), 7.23 (d, 2.0 Hz, 1H), 2.71 (s, 2H), 2.30 (s, 2H), 1.02 (s, 6H)

4-oxo-4,5,6,7-tetrahydroindole-2-carboxaldehyde

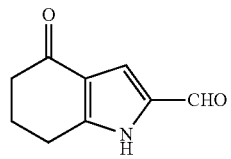

By using a procedure analogous to preparation of 6,6-dimethyl-4-oxo-4,5,6,7-tetrahydroindole-2-carboxaldehyde, 1,3-cyclohexane dione 4.55 g (39.36 mmol) was condensed with D-glucosamine HCl 6.84 g (31.72 mmol) in water 40 mL in the presence of sodium carbonate 1.683 g, at ambient temperature for 11 days. (The polyol intermediate did not crystallize). The reaction mixture was extracted twice with chloroform (2×100 mL) and the aqueous phase was retained. The organic phases were back-extracted with water 150 mL. The combined aqueous phases were cooled in a 1 L flask on ice, solid sodium periodate 35.0 g (160 mmol) was gradually added over 10 minutes and the reaction was continued for additional 20 minutes on ice. The mixture was them made basic by gradual addition of saturated sodium bicarbonate solution 80 mL (foaming) and the stirring was continued for 30 minutes. The reaction mixture was filtered, the solids were washed with chloroform 0.5 L. The biphasic filtrates were shaken and separated, the aqueous phase was re-extracted with additional chloroform 0.5 L. The combined organic extracts were dried ($MgSO_4$) and evaporated. The obtained crystalline residue was suspended in benzene (10 mL), collected by filtration, washed with benzene and dried. Y=534 mg (10% overall) of a pale yellow solid. 1H-NMR (d6-DMSO, 400 MHz): 12.50 (br s, 1H), 9.51 (s, 1H), 7.23 (d, 2.0 Hz, 1H), 2.81 (t, 6.3 Hz, 2H), 2.39 (dd, 6.8 Hz, 5.8 Hz, 2H), 2.03 (quint, 6.2 Hz, 2H)

General Procedure A, for the Condensation of tetrahydroindole-2-carboxaldehydes with Oxindoles

Example 1

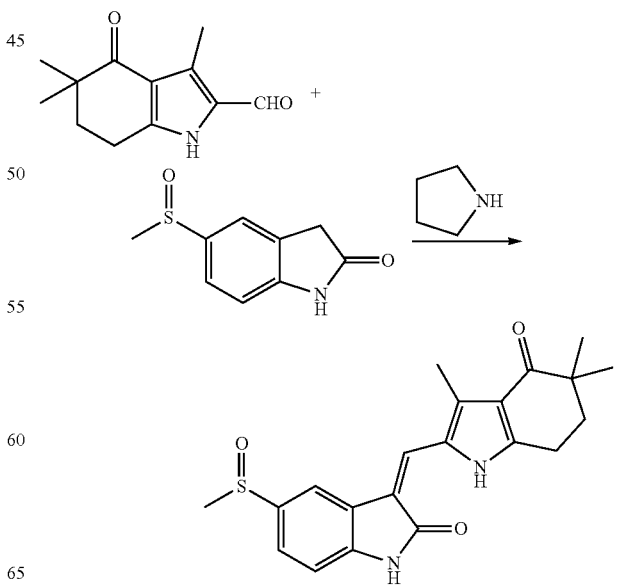

The substituted 4,5,6,7-tetrahydroindole-2-carboxaldehyde 0.50 mmol (103 mg of 3,5,5-trimethyl-4-oxo-4,5,6,7-tetrahydroindole-2-carboxaldehyde) and substituted oxindole 0.50 mmol (98 mg of 5-methylsulfoxyoxyndole) was refluxed in ethanol in the presence of catalytic amount of pyrrolidine 10 μL for 2 hours. The cooled reaction mixture was acidified with addition of 2 drops of 6M HCl and the precipitated orange product was collected by filtration, washed with cold methanol and dried. The typical yield for this and related examples was 60-95% of theory. The obtained products were pure by HPLC, LC-MS and NMR.

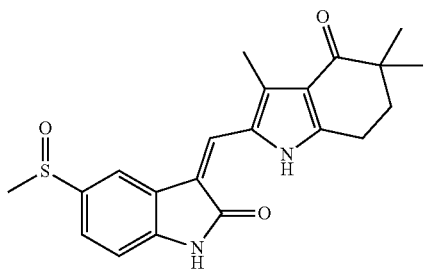

65% yield (125 mg of an orange microcrystalline solid) 1H (d6-DMSO, 400 MHz): 13.64 (s, 1H), 11.28 (s, 1H), 8.22 (s, 1H), 7.88 (s, 1H), 7.49 (dd, 8.1 Hz, 1.5 Hz, 1H), 7.05 (d, 8.1 Hz, 1H), 2.96 (t, 6.1 Hz, 2H), 2.77 (s, 3H), 2.55 (s, 3H), 1.94 (t, 6.1 Hz, 2H), 1.10 (s, 6H); 13C (d6-DMSO, 100 MHz): 198.71, 169.45, 146.56, 140.71, 138.67, 131.02, 127.81, 126.17, 125.01, 122.74, 118.37, 115.89, 115.08, 109.89, 99.51, 43.26, 41.75, 36.13, 24.26, 19.90, 10.87

Examples 2-16 used entirely analogous procedures to example 1, using the appropriate aldehyde and/or oxindole precursors.

Example 2

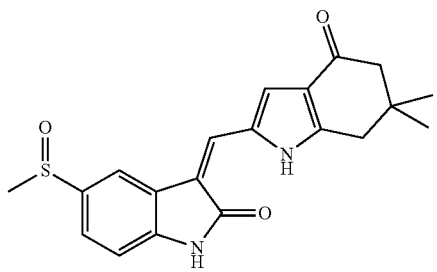

1H (d6-DMSO, 400 MHz): 13.43 (s, 1H), 11.32 (s, 1H), 8.02 (d, 1.5 Hz, 1H), 7.97 (s, 1H), 7.49 (dd, 8.1 Hz, 1.8 Hz, 1H), 7.09 (d, 1.8 Hz, 1H), 7.06 (d, 7.8 Hz, 1H), 2.98 (s, 2H), 2.75 (s, 3H), 2.33 (s, 2H), 1.06 (s, 6H)

Example 3

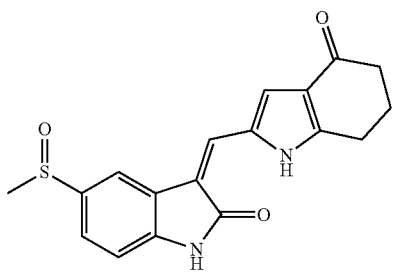 [SMILES: CS(=O)c1ccc2c(c1)/C(=C/c1cc3c([nH]1)CCCC3=O)C(=O)N2]

1H (d6-DMSO, 400 MHz): 13.42 (s, 1H), 11.32 (s, 1H), 8.02 (d, 1.8 Hz, 1H), 7.98 (s, 1H), 7.49 (dd, 8.3 Hz, 1.8 Hz, 1H), 7.07 (m, 2H), 2.97 (t, 6.3 Hz, 2H), 2.75s (s, 3H), 2.42 (t, 6.2 Hz, 2H), 2.08 (m, 2H)

Example 4

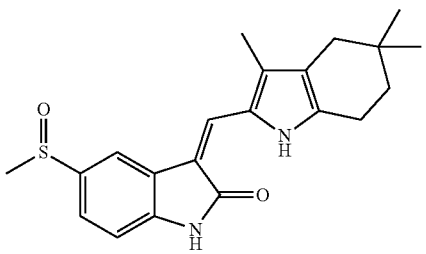

1H (d6-DMSO, 400 MHz): 13.31 (br s, 1H), 11.05 (s, 1H), 8.10 (s, 1H), 7.76 (s, 1H), 7.40 (dd, 8.1 Hz, 1.5 Hz, 1H), 7.02 (d, 8.1 Hz, 1H), 2.76 (s, 3H), 2.70 (t, 6.5 Hz, 2H), 2.24 (s, 3H), 2.23 (br s, 2H), 1.57 (t, 6.5 Hz, 2H), 0.98 (s, 6H); 13C (d6-DMSO, 100 MHz): 169.28, 139.69, 137.91, 136.55, 130.04, 127.08, 124.87, 120.99, 120.92, 113.67, 110.48, 109.38, 43.3, 34.92, 29.82, 27.87, 20.24, 9.28

Example 5

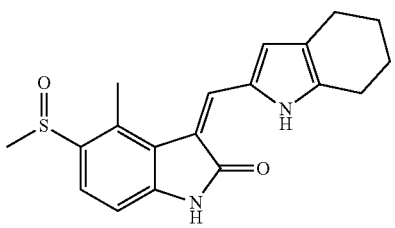 [SMILES: Cc1c(S(C)=O)ccc2c1/C(=C/c1cc3c([nH]1)CCCC3)C(=O)N2]

1H (d6-DMSO, 400 MHz): 13.25 (br s, 1H), 11.08 (s, 1H), 7.67 (s, 1H), 7.59 (d, 8.1 Hz, 1H), 7.01 (d, 8.1 Hz, 1H), 6.75 (s, 1H), 2.72 (br m, 2H), 2.65 (s, 3H), 2.58 (s, 3H), 2.53 (br m, 2H), 1.78 (br m, 2H), 1.72 (br m, 2H)

Example 6

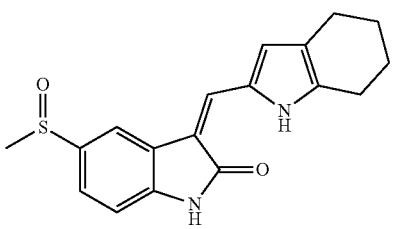

(1:1 solvate with ethanol)

1H (d6-DMSO, 400 MHz): 13.10 (br s, 1H), 11.07 (s, 1H), 7.95 (d, 1.5 Hz, 1H), 7.80 (s, 1H), 7.41 (dd, 8.0 Hz, 1.6 Hz, 1H), 7.03 (d, 8.0 Hz, 1H), 6.67 (br s, 1H), 4.34 (t, 5.1 Hz, 1H), 3.44 (m, 2H), 2.74 (s, 3H), 2.72 (br m, 2H), 2.53 (br m, 2H), 1.79 (m, 2H), 1.72 (m, 2H), 1.06 (t, 7.0 Hz, 3H)

Example 7

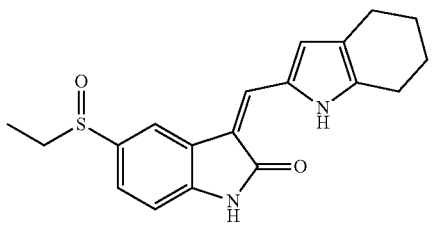 [SMILES: CCS(=O)c1ccc2c(c1)/C(=C/c1cc3c([nH]1)CCCC3)C(=O)N2]

1H (d6-DMSO, 400 MHz): 13.10 (br s, 1H), 11.07 (s, 1H), 7.89 (d, 1.2 Hz, 1H), 7.79 (s, 1H), 7.35 (dd, 8.0 Hz, 1.6 Hz, 1H), 7.03 (d, 8.0 Hz, 1H), 6.66 (br s, 1H), 2.95 (m, 1H), 2.79 (m, 1H), 2.73 (br m, 2H), 2.53 (br m, 2H), 1.78 (m, 2H), 1.72 (m, 2H), 1.04 (t, 7.4 Hz, 3H)

Example 8

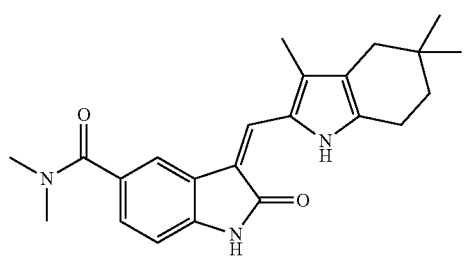

1H (d6-DMSO, 400 MHz): 13.29 (s, 1H), 10.91 (s, 1H), 7.85 (d, 1.3 Hz, 1H), 7.70 (s, 1H), 7.12 (dd, 8.1 Hz, 1.5 Hz, 1H), 6.88 (d, 7.8 Hz, 1H), 2.98 (s, 6H), 2.68 (t, 6.3 Hz, 2H), 2.21 (s, 5H), 1.56 (t, 6.3 Hz, 2H), 0.98 (s, 6H); 13C (d6-DMSO, 100 MHz): 170.81, 169.39, 138.43, 135.71, 129.37, 128.99, 127.01, 125.84, 124.43, 124.33, 120.59, 117.17, 111.22, 108.45, 35.05, 34.95, 29.83 (2C), 27.88, 20.22, 9.24 (2C)

Example 9

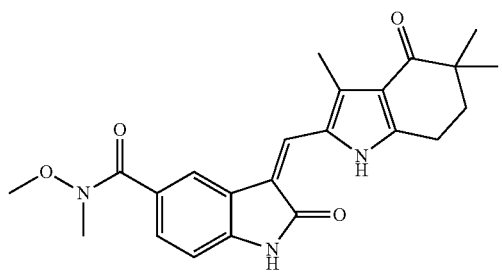 [SMILES: CCN(C)C(=O)c1ccc2c(c1)/C(=C/c1[nH]c3c(c1C)C(=O)C(C)(C)CC3)C(=O)N2]

1H (d6-DMSO, 400 MHz): 13.65 (s, 1H), 11.22 (s, 1H), 8.11 (d, 1.3 Hz, 1H), 7.83 (s, 1H), 7.43 (dd, 8.1 Hz, 1.8 Hz, 1H), 6.93 (d, 7.8 Hz, 1H), 3.57 (s, 3H), 3.27 (s, 3H), 2.95 (t, 6.3 Hz, 2H), 2.54 (s, 3H), 1.94 (t, 6.3 Hz, 2H), 1.10 (s, 6H)

Example 10

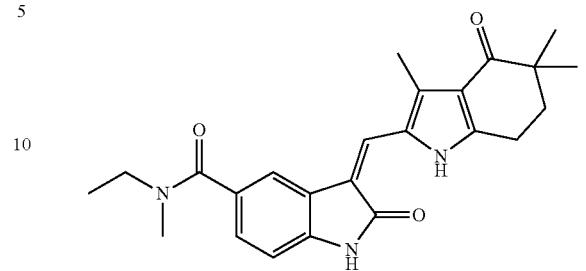

1H (d6-DMSO, 400 MHz): 13.68 (s, 1H), 11.15 (s, 1H), 7.96 (s, 1H), 7.84 (s, 1H), 7.17 (br d, 7.3 Hz, 1H), 6.91 (d, 8.1 Hz, 1H), 3.45 (very br s, 1H), 3.29 (very br s, 1H), 2.95 (m, 5H), 2.53 (s, 3H), 1.94 (t, 6.3 Hz, 2H), 1.10 (br s, 9H)

Example 11

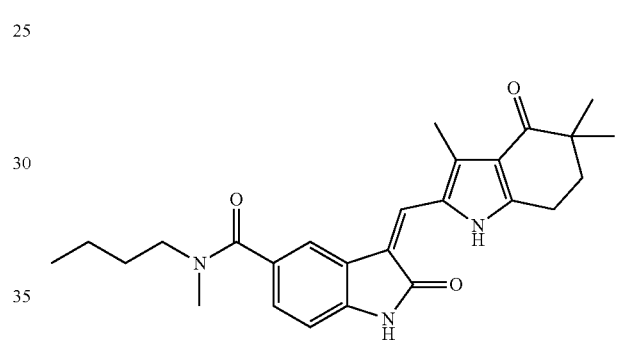

1H (d6-DMSO, 400 MHz): 13.68 (s, 1H), 11.15 (s, 1H), 7.94 (d, 1.0 Hz, 1H), 7.83 (s, 1H), 7.16 (br d, 7.6 Hz, 1H), 6.91 (d, 7.8 Hz, 1H), 3.42 (very br s, 1H), 3.27 (very br s, 1H), 2.94 (m, 5H), 2.53 (s, 3H), 1.94 (t, 6.2 Hz, 2H), 1.55 (very br s, 2H), 1.33 (very br m, 1H), 1.10 (br s, 6H), 0.94-0.73 (very br m, 3H)

Example 12

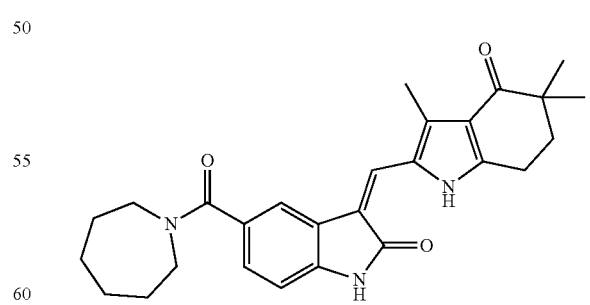

1H (d6-DMSO, 400 MHz): 13.69 (s, 1H), 11.13 (s, 1H), 7.95 (d, 1.2 Hz, 1H), 7.84 (s, 1H), 7.15 (dd, 7.8 Hz, 1.6 Hz, 1H), 6.90 (d, 7.8 Hz, 1H), 3.56 (br t, 5.9 Hz, 2H), 3.39 (br t, 5.8 Hz, 2H), 2.95 (t, 6.1 Hz, 2H), 2.53 (s, 3H), 1.94 (t, 6.2 Hz, 2H), 1.74 (br m, 2H), 1.56 (br m, 6H), 1.10 (s, 6H)

Example 13

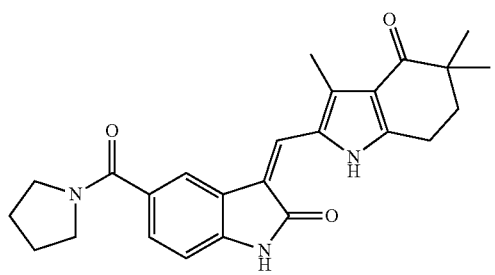 [SMILES: Cc1c(/C=C2\C(=O)Nc3ccc(C(=O)N4CCCC4)cc32)[nH]c2c1C(=O)C(C)(C)CC2]

1H (d6-DMSO, 400 MHz): 13.67 (s, 1H), 11.17 (s, 1H), 8.07 (d, 1.2 Hz, 1H), 7.83 (s, 1H), 7.33 (dd, 7.8 Hz, 1.5 Hz, 1H), 6.91 (d, 7.8 Hz, 1H), 3.47 (t, 6.3 Hz, 4H), 2.95 (t, 6.3 Hz, 2H), 2.54 (s, 3H), 1.94 (t, 6.3 Hz, 2H), 1.87 (m, 2H), 1.82 (m, 2H), 1.10 (s, 6H)

Example 14

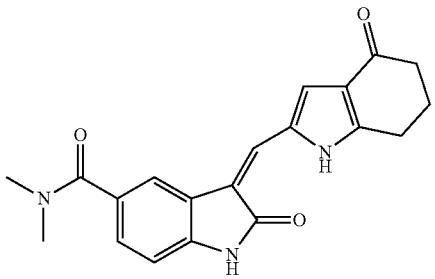 [SMILES: CN(C)C(=O)c1ccc2c(c1)/C(=C/c1cc3c([nH]1)CCCC3=O)C(=O)N2]

1H (d6-DMSO, 400 MHz): 13.44 (br s, 1H), 11.20 (s, 1H), 7.92 (s, 1H), 7.75 (s, 1H), 7.26 (dd, 7.8 Hz, 1.5 Hz, 1H), 7.00 (d, 1.8 Hz, 1H), 6.93 (d, 8.1 Hz, 1H), 2.99 (s, 6H), 2.96 (app t, 6.1 Hz, 2H), 2.42 (app t, 6.0 Hz, 2H), 2.08 (m, 2H)

Example 15

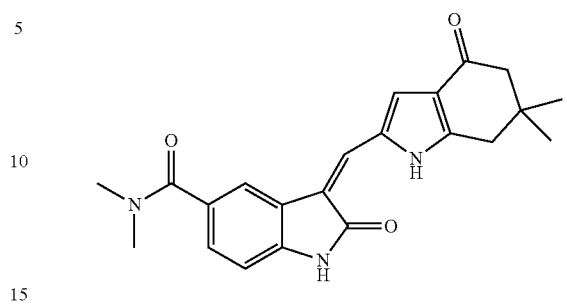

1H (d6-DMSO, 400 MHz): 13.45 (br s, 1H), 11.20 (s, 1H), 7.91 (s, 1H), 7.75 (s, 1H), 7.26 (dd, 7.8 Hz, 1.3 Hz, 1H), 7.02 (d, 1.3 Hz, 1H), 6.93 (d, 7.8 Hz, 1H), 2.99 (s, 6H), 2.87 (s, 2H), 2.32 (s, 2H), 1.06 (s, 6H); 13C (d6-DMSO, 100 MHz): 192.34, 170.27, 169.30, 147.05, 140.00, 130.24, 129.56, 126.92, 126.85, 124.49, 121.10, 118.52, 118.30, 116.01, 109.18, 51.68, 36.23, 35.14 (2C), 28.01 (2C)

Example 16

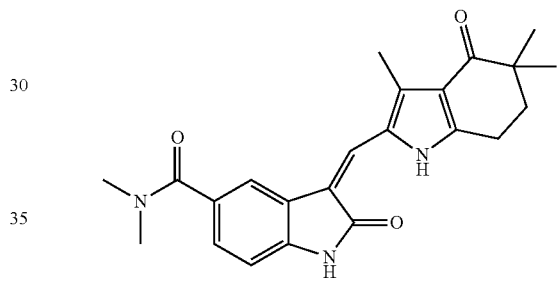

1H (d6-DMSO, 400 MHz): 13.62 (s, 1H), 11.16 (s, 1H), 7.98 (d, 1.3 Hz, 1H), 7.83 (s, 1H), 7.21 (dd, 8.1 Hz, 1.8 Hz, 1H), 6.91 (d, 7.8 Hz, 1H), 2.99 (s, 6H), 2.95 (t, 6.1 Hz, 2H), 2.53 (s, 3H), 1.94 (t, 6.1 Hz, 2H), 1.10 (s, 6H); 13C (d6-DMSO, 100 MHz): 198.69, 170.47, 159.56, 146.18, 139.40, 130.39, 129.64, 127.81, 126.14, 124.94, 124.38, 118.41, 118.26, 116.54, 108.98, 41.73 (2C), 36.19, 24.27, 19.89, 10.79

General Procedure B, for the Condensation of 2-formyl-3,5-dimethylpyrrole-4-carboxylic acid with Oxindoles and the Side Chain Attachment

Example 17

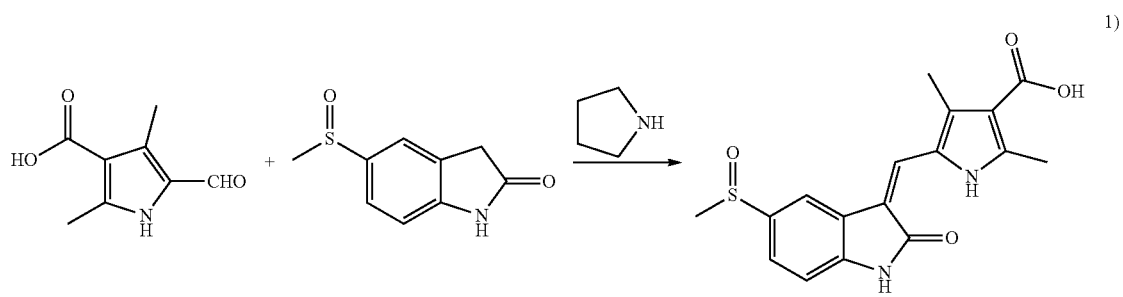

1)

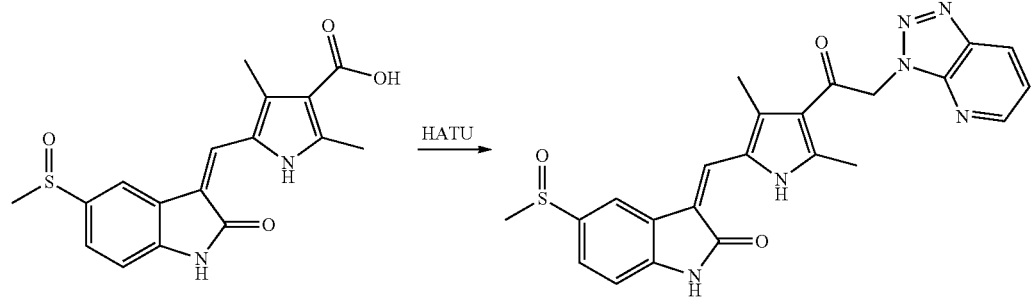

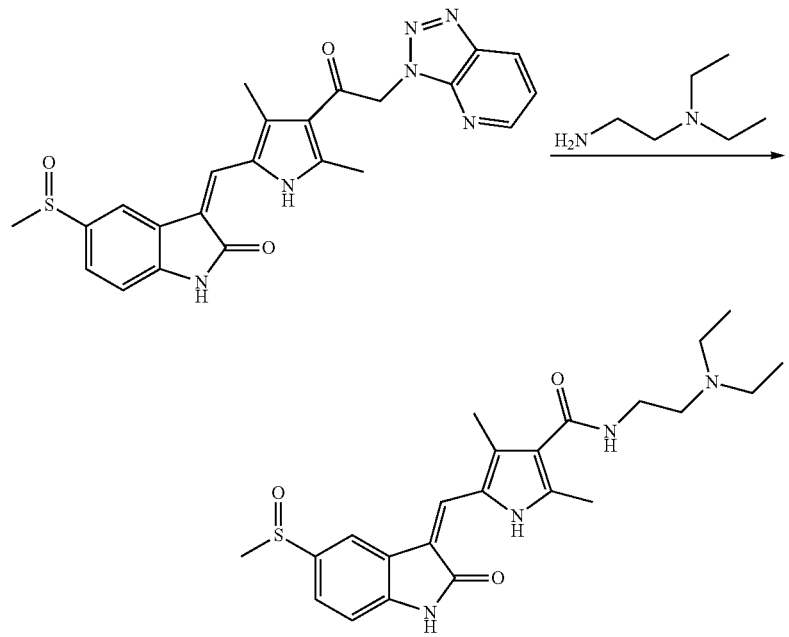

1) A mixture of 3,5-dimethyl-2-formylpyrrole-4-carboxylic acid 1.50 mmol (251 mg) and 1.54 mmol of the substituted oxindole (294 mg of 5-methylsulfoxyoxindole) in ethanol 15 mL was treated with a catalytic amount of pyrrolidine 30 microliters and the mixture was refluxed for 3 hours. The reaction mixture was acidified with 4 drops of 6M HCl and cooled to ambient temperature. The precipitated carboxylic acid intermediate was collected by filtration, washed with methanol and thoroughly dried. The typical yield of this step was 90-98% of theory (90% for 5-methylsulfoxyoxindole).

2) A slurry of the carboxylic acid intermediate from the Step 1, 1.413 mmol in anhydrous DMF 15 mL, was stirred for 15 minutes. Diisopropylethylamine 0.5 mL was added and the mixture was stirred for additional 10 minutes. Solid HATU coupling reagent 510 mg (1.34 mmol) was then added into the vigorously stirred reaction mixture. The mixture became homogenous and then a new precipitate gradually formed. After one hour stirring, the reaction mixture was diluted with anhydrous acetonitrile 80 mL and the stirring was continued for another one hour. The precipitated azabenztriazolyl active ester was collected by filtration, washed with acetonitrile and dried. The typical yield was 60-98% of theory (60% for 5-methylsulfoxyoxindole).

3) A slurry of the active ester from the Step 2, 0.400 mmol in anhydrous dimethylacetamide 3 mL was treated with N,N-diethylethylenediamine 65 microliters. The mixture was stirred to complete dissolution (15 minutes) and then evaporated on highvac. The obtained oily residue was dissolved in 4 mL of a 5% diethylamine solution in methanol. The mixture was placed into a refrigerator overnight. The precipitated deep orange-colored product was collected by filtration, washed with a small volume of chilled methanol, dried by suction and then on highvac. The typical yield of the last step was 60-95% of theory (64.5% for 5-methylsulfoxyoxindole). The obtained products were pure by HPLC, LC-MS and NMR. (5% diisopropylamine in MeOH instead of diethylamine is also acceptable for the workup).

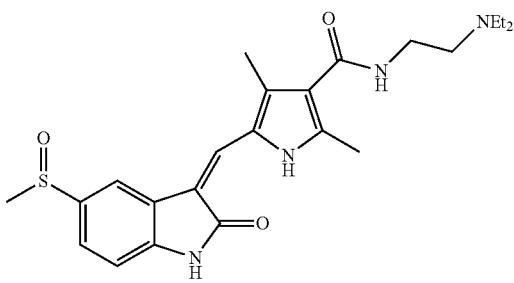

1H (d6-DMSO, 400 MHz): 13.62 (br s, 1H), 11.17 (s, 1H), 8.18 (d, 1.2 Hz, 1H), 7.83 (s, 1H), 7.45 (m, 2H), 7.05 (d, 8.1 Hz, 1H), 3.30 (m, 2H), 2.77 (s, 3H), 2.53 (m, 6H), 2.46 (s, 3H), 2.45 (s, 3H), 0.98 (t, 7.1 Hz, 6H)

2H), 3.40 (br m, 2H), 3.28 (q, 6.8 Hz, 2H), 2.50 (m, 6H), 2.44 (s, 3H), 2.43 (s, 3H), 1.74 (br m, 2H), 1.56 (br m, 6H), 0.97 (t, 7.1 Hz, 6H)

Example 18

Example 21

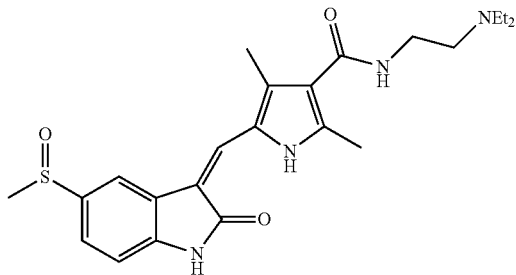

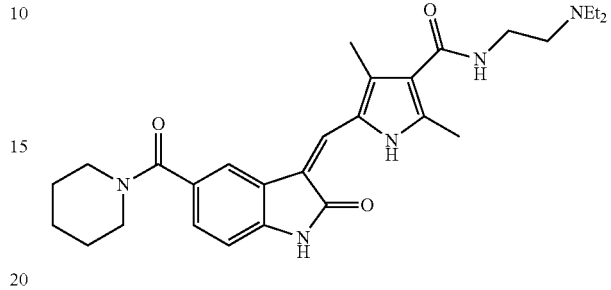

1H (d6-DMSO, 400 MHz): 13.62 (br s, 1H), 11.18 (s, 1H), 7.64 (s, 1H), 7.61 (d, 8.1 Hz, 1H), 7.45 (t, 5.5 Hz, 1H), 7.03 (d, 8.1 Hz, 1H), 3.28 (m, 2H), 2.66 (s, 3H), 2.62 (s, 3H), 2.52 (m, 6H), 2.451 (s, 3H), 2.35 (s, 3H), 0.97 (t, 7.1 Hz, 6H)

1H (d6-DMSO, 400 MHz): 13.64 (s, 1H), 11.05 (s, 1H), 7.89 (d, 1.3 Hz, 1H), 7.76 (s, 1H), 7.43 (t, 5.8 Hz, 1H), 7.12 (dd, 7.8 Hz, 1.5 Hz, 1H), 6.90 (d, 7.8 Hz, 1H), 3.46 (very br m, 4H), 3.28 (q, 6.8 Hz, 2H), 2.50 (m, 6H), 2.45 (s, 3H), 2.43 (s, 3H), 1.62 (m, 2H), 1.51 (br s, 4H), 0.97 (7.1 Hz, 6H)

Example 19

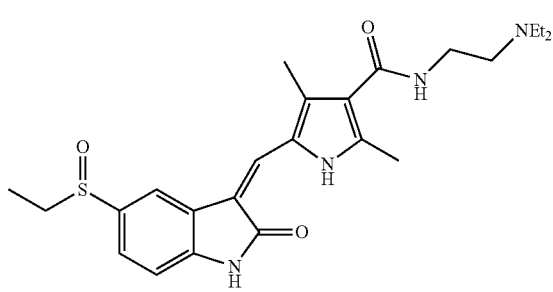

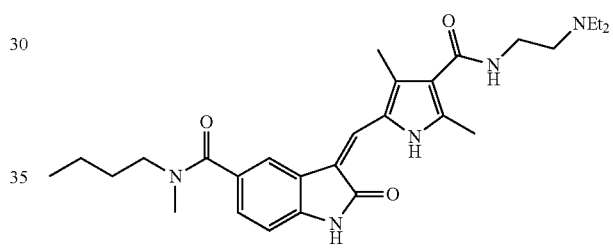

1H (d6-DMSO, 400 MHz): 13.62 (br s, 1H), 11.18 (s, 1H), 8.13 (s, 1H), 7.82 (s, 1H), 7.46 (br t, 4.9 Hz, 1H), 7.40 (d, 7.8 Hz, 1H), 7.05 (d, 8.0 Hz, 1H), 3.30 (m, 2H), 2.98 (m, 1H), 2.84 (m, 1H), 2.53 (m, 6H), 2.46 (br s, 6H), 1.06 (t, 7.2 Hz, 3H), 0.98 (t, 7.0 Hz, 6H)

1H (d6-DMSO, 400 MHz): 13.61 (s, 1H), 11.05 (s, 1H), 7.89 (s, 1H), 7.77 (s, 1H), 7.43 (t, 5.8 Hz, 1H), 7.13 (d, 7.6 Hz, 1H), 6.90 (d, 7.8 Hz, 1H), 3.41 (very br s, 2H), 3.28 (q, 6.5 Hz, 2H), 2.94 (s, 3H), 2.50 (m, 6H), 2.45 (s, 3H), 2.43 (s, 3H), 1.55 (br m, 2H), 1.34-0.76 (br m, 5H), 0.97 (t, 7.1 Hz, 6H)

Example 20

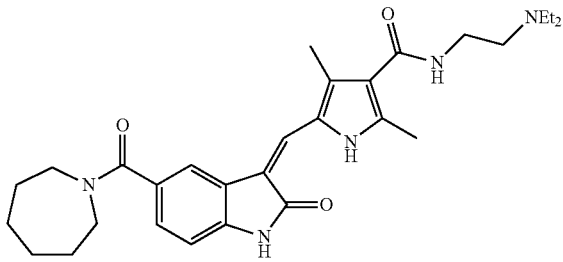

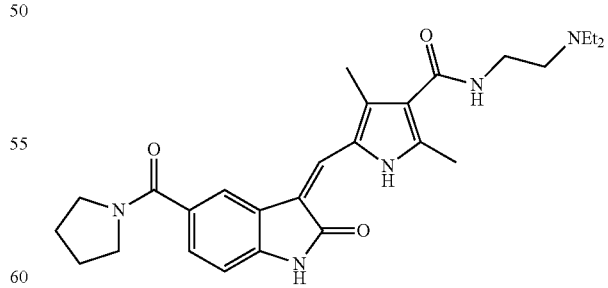

1H (d6-DMSO, 400 MHz): 13.65 (s, 1H), 11.03 (s, 1H), 7.89 (d, 1.3 Hz, 1H), 7.77 (s, 1H), 7.43 (t, 5.6 Hz, 1H), 7.11 (dd, 7.8 Hz, 1.5 Hz, 1H), 6.89 (d, 7.8 Hz, 1H), 3.55 (br m, 1H (d6-DMSO, 400 MHz): 13.63 (s, 1H), 11.07 (s, 1H), 8.02 (s, 1H), 7.77 (s, 1H), 7.43 (t, 5.6 Hz, 1H), 7.29 (dd, 8.1 Hz, 1.1 Hz, 1H), 6.90 (d, 8.1 Hz, 1H), 3.47 (t, 6.6 Hz, 4H), 3.28 (q, 6.8 Hz, 2H), 2.44 (s, 3H), 2.43 (s, 3H), 1.85 (m, 4H), 0.97 (t, 7.1 Hz, 6H)

Example 24
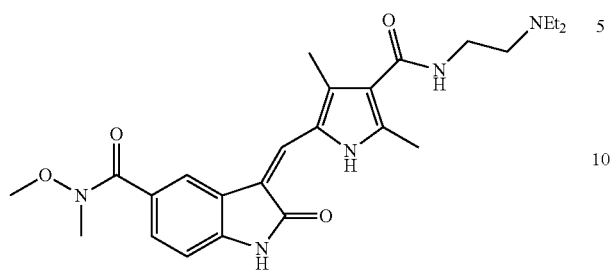
1H (d6-DMSO, 400 MHz): 13.62 (s, 1H), 11.12 (s, 1H), 8.06 (d, 1.3 Hz, 1H), 7.76 (s, 1H), 7.44 (t, 5.8 Hz, 1H), 7.40 (dd, 8.1 Hz, 1.5 Hz, 1H), 6.92 (d, 8.1 Hz, 1H), 3.57 (s, 3H), 3.29 (m, 2H), 3.27 (s, 3H), 2.50 (m, 6H), 2.45 (s, 3H), 2.43 (s, 3H), 0.98 (t, 7.1 Hz, 6H)
Example 25
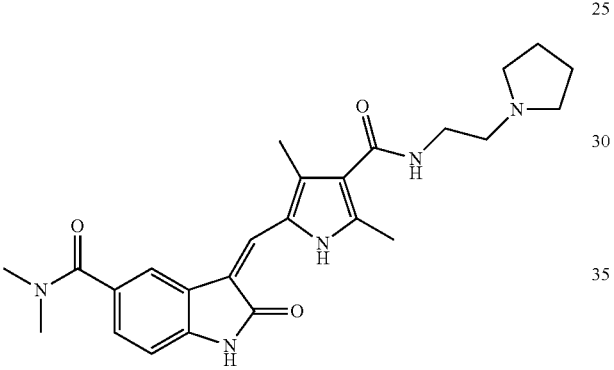
1H (d6-DMSO, 400 MHz): 13.62 (s, 1H), 11.06 (s, 1H), 7.92 (s, 1H), 7.76 (s, 1H), 7.54 (t, 5.6 Hz, 1H), 7.17 (dd, 7.8 Hz, 1.8 Hz, 1H), 6.90 (d, 7.8 Hz, 1H), 3.32 (m, 2H), 2.98 (s, 6H), 2.56 (t, 6.9 Hz, 2H), 2.48 (m, 4H), 2.43 (s, 3H), 2.41 (s, 3H), 1.68 (m, 4H)
Example 26
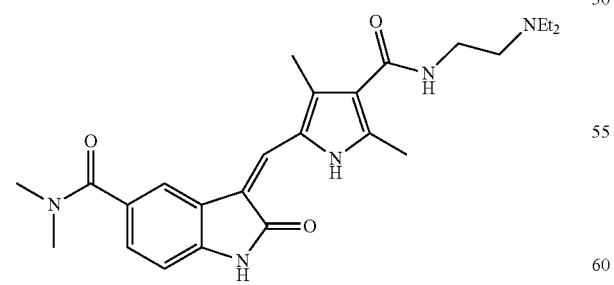
1H (d6-DMSO, 400 MHz): 13.63 (s, 1H), 11.04 (s, 1H), 7.93 (s, 1H), 7.77 (s, 1H), 7.42 (br t, 5.4 Hz, 1H), 1.18 (dd, 8.0 Hz, 1.2 Hz, 1H), 6.91 (d, 8.0 Hz, 1H), 3.30 (m, 2H), 2.99 (s, 6H), 2.53 (m, 6H), 2.45 (s, 3H), 2.43 (s, 3H), 0.98 (t, 7.1 Hz, 6H)
Example 27
Additional Compounds
The following additional compounds were prepared by analogous methods:
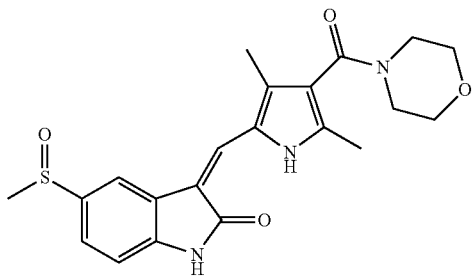
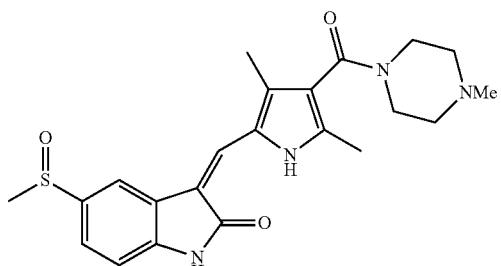
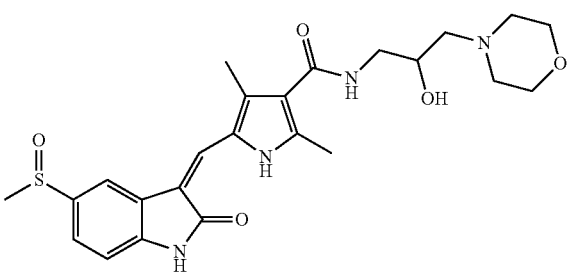
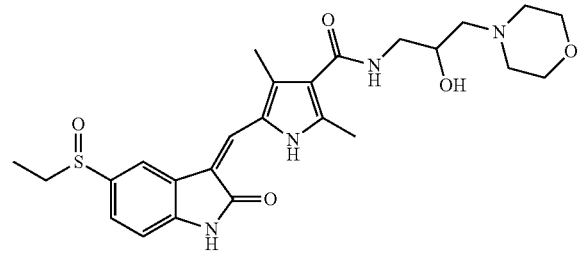
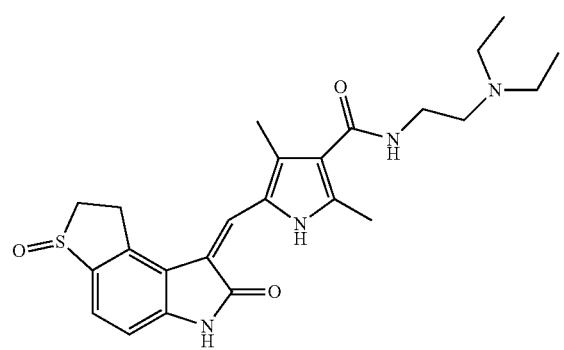

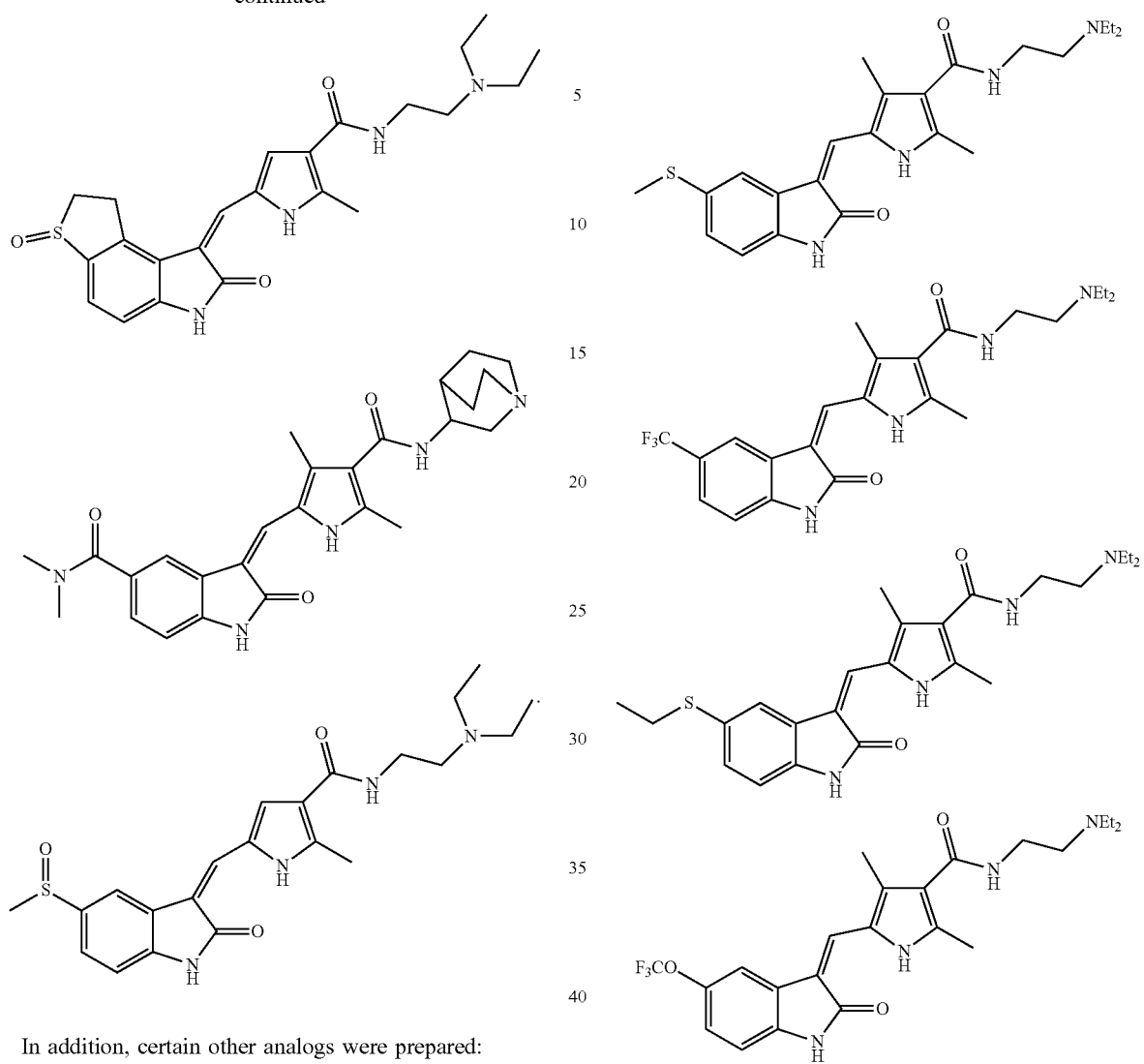
In addition, certain other analogs were prepared:
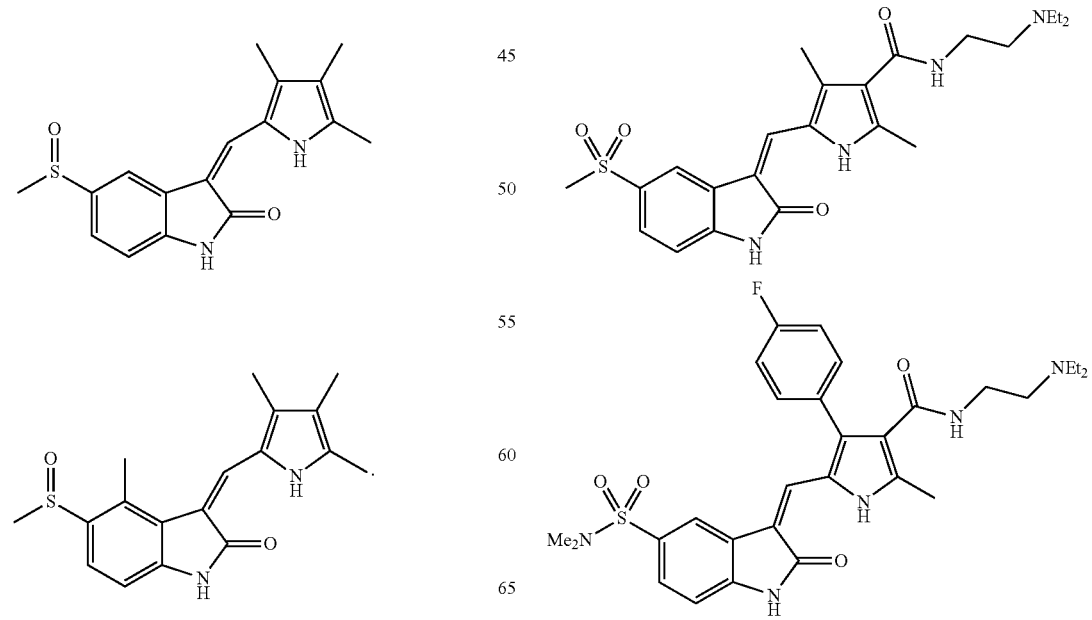

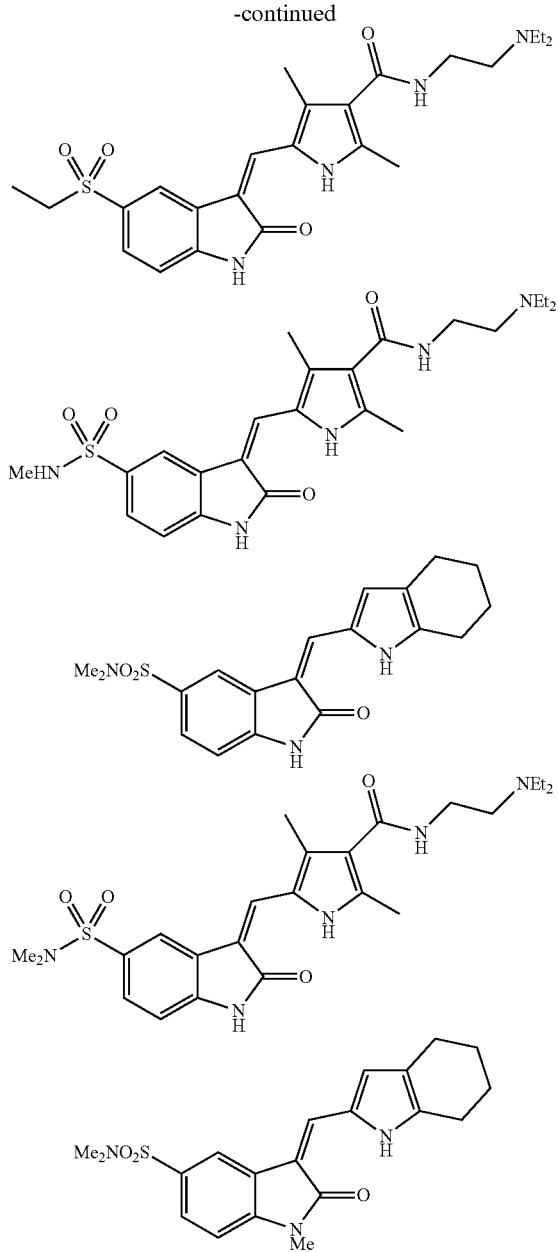

All compounds were prepared in purified form and their spectroscopic data were consistent with their structures.

Example 28

Neuroprotective Compound Treatment Increases RGC Count and Neurite Length In Vitro In this Example, certain compounds were administered to retinal ganglion cells (RGCs) in cell culture to determine the effects of the compounds on neuronal count and neurite growth.

We established a robust high-content screening system combining the immunopanning- or other immunobead-based purification of primary mouse and rat RGCs and automated fluorescence-based imaging analysis (see, e.g., U.S. Patent Publication No. 2007/0185069, incorporated herein by reference). To enhance the assay sensitivity, the culture condition is defined to support a baseline level of RGC viability (20~60% surviving RGCs after three days in culture) and neurite growth by 2.5 µM forskolin.

Certain tested compounds showed activity in promoting RGC survival. In addition, certain tested compounds stimulated RGC neurite growth. Representative data are shown below:

| Compound (Example) | RGC Survival Activity | Neurite Promotion |
|---|---|---|
| 2 | *** | |
| 3 | *** | |
| 5 | * | ** |
| 6 | *** | |
| 7 | *** | |
| 8 | ** | |
| 9 | *** | |
| 10 | *** | |
| 11 | ** | |
| 12 | ** | |
| 13 | *** | |
| 14 | *** | |
| 15 | ** | |
| 16 | *** | |
| 17 | *** | *** |
| 18 | *** | *** |
| 19 | *** | |
| 23 | *** | |
| 24 | *** | |
| 25 | *** | |
| 26 | *** | |
| | ** | |
| | * | |

Key:
***: at least approximately 80% as potent as sunitinib
**: approximately 40-80% as potent as sunitinib
*: approximately 10-40% as potent as sunitinib
0: less than approximately 10% as potent as sunitinib See also PCT Patent Publication No. WO 2010/017541 for sunitinib.

Example 29

Assay for Compounds Capable of Protecting Against NMDA Excitotoxicity In Vitro

Neuronal toxicity of excitatory amino acid glutamate and its analogue NMDA is implicated in a number of neurodegenerative conditions that involve RGC, such as glaucoma, optic neuropathies of trauma and other origins, and that affect other CNS structures, such as Alzheimer's disease, Parkinson's disease, Huntington's disease, stroke, and amyloid lateral sclerosis (ALS). Although the vulnerability of rodent RGC to excitotoxicity has been demonstrated in many in vitro and in vivo studies, there are a few reports suggesting that rodent RGCs may be resistant to glutamate excitotoxicity. The compounds of the invention can be screened to determine whether they can render primary mouse RGC resistance to glutamate excitotoxicity.

Purified mouse RGCs are seeded with or without 1 µM test compound for 16 hours prior to a 5-hour exposure to three different concentrations (100 µM, 250 µM, 500 µM) of glutamate, kainite acid (KA), NMDA, and AMPA. RGC viability is measured and the percentage of RGC loss due to the excitotoxicity is calculated. All four excitatory glutamate receptor agonists show strong and dosage-dependent damage to mouse RGC at these relatively high concentrations. A test compound capable of antagonizing the detrimental effect of glutamate and its analogues (i.e., by reducing the RGC loss caused by 100 µM of NMDA and AMPA) has potential therapeutic value in the management of excitotoxicity-associated neurodegenerative conditions.

Example 30

Assay for Compounds Capable of Protecting Against Axon-Injury Induced RGC Cell Death In Vivo Mouse optic nerve crush is a well-established animal model in mimicking the pathological conditions in which the primary injury sites are focal to RGC axons such as in glaucoma, AION, traumatic optic neuropathy, and multiple sclerosis. Specific RGC loss following nerve crush, which largely spares displaced amacrine cells in GCL, is thought to result from incomplete understood mechanism that implicates the blockage of retrograde axonal transport and subsequently impaired neurotrophin signaling, and excitotoxicity etc. In addition, mouse optic nerve crush has been successfully employed as an experimental system to identify the genetic nature controlling RGC susceptibility to axon injury.

In a representative assay procedure, the optic nerve is carefully exposed through a post-orbital approach, and crushed with a self-closing forceps for three seconds. This typically results in an ~25.2% of cell loss in GCL within ten days. Since RGCs populate ~60% cells in rodent GCL, the estimated surviving RGC is ~57.3%. Optic nerves are treated at five different dosages (5, 10, 15, 20, 40 mg/kg/day). An increase in RGC survival with the systemic administration of a test compound suggests that the compound can protect mouse RGCs from axon injury induced cell death.

Apoptosis has been identified as the major form of RGC death in many, if not all, degenerative conditions targeting their axons, and in mouse optic nerve. The neuroprotective activity of the compounds of the invention may be related, at least in part, to the ability to block or attenuate the activation of apoptotic pathway(s).

Example 31

Assay for Compounds Capable of Attenuating or Reversing Potential Detrimental Signals from RTK Ligand(s)

To examine whether test compounds can attenuate or reverse potential detrimental signals from RTK ligand(s), the following assay can be performed.

FLT3 ligand (Flt3l) at 16 ng/ml, a concentration four times its EC50, can reduce RGC survival by 38.3%, but does not do so at its EC50 of 4 ng/ml. A test compound can be added to the media; antagonization of the detrimental effects of FLT3l at suggests that the test compound may have neuroprotective activity.

Example 32

Assay for Compounds Capable of Increasing RGC Survival

Mouse retinal ganglion cells (RGCs) are purified and then are grown in culture for approximately 2 days in the presence or absence of various concentrations of test compound. At the end of the culture period, live-dead and neurite outgrowth assays are performed and the stained cells are analyzed with a Cellomics VTI HCS reader and Cellomics image analysis software.

Example 33

Evaluation of Protective Effects

Based on a combination of microarray, kinase profiling studies, and phospho-western blot analysis of retinal ganglion cells treated with sunitinib and its analogs, the growth survival promoting activity of the compounds of the invention appears to be mediated through kinase inhibition of the following signaling pathways: JNK1-3, the MAP2Ks, TAK1, RIPK1-3, CDKs, MLCK, HPK1, RET, LCK, LRRK, GSK3, RAP, SRC kinases, STE20 kinases, and trkA. Through modulation of these kinases signaling pathways, survival is partially mediated by stimulation of AKT and the mTOR pathway and associated inhibition of autophagy, and reduced endoplasmic reticular stress. Without wishing to be bound by theory, it is believed that observed toxicity at higher concentrations of such compounds is mediated, in part, by a reverse effect, inhibition of Akt/mTOR activation. One approach to expanding the therapeutic window of these compounds is to reduce the toxicity seen at high dosages that is due to inhibition of Akt/mTOR activation. The sulfoxide-containing compounds of the invention do show less inhibition of Akt/mTOR activation at high concentrations and also show less toxicity, demonstrating that the approach described here can lead to improved and safer neuroprotective agents.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of therapeutically treating macular degeneration in a subject in need thereof, the method comprising administering to a subject in need thereof an effective amount of a compound of formula (I) or formula (II):

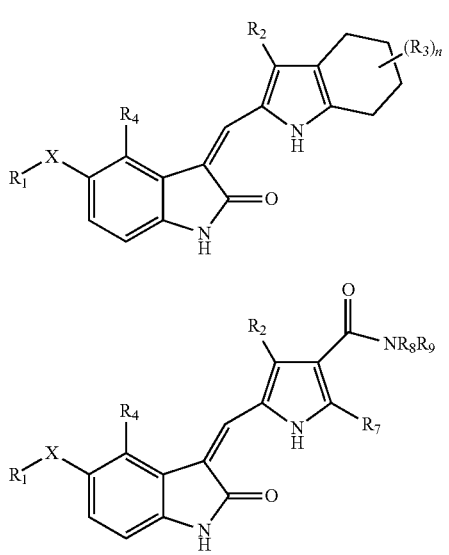

wherein:
X is S(O);
$R_1$ is substituted or unsubstituted $C_1$-$C_6$ alkyl, $C_3$-$C_6$ cycloalkyl or allyl;
$R_2$ is H or substituted or unsubstituted $C_1$-$C_6$ alkyl, $C_3$-$C_6$ cycloalkyl or allyl;
$R_3$ is selected, independently for each occurrence, from the group consisting of substituted or unsubstituted $C_1$-$C_6$ alkyl, $C_3$-$C_6$ cycloalkyl, allyl, substituted or unsubstituted $C_1$-$C_6$ alkoxy, aryl, cyano, halogen, hydroxy, oxo, amino, or —C(O)—$R_a$, in which $R_a$ is substituted or unsubstituted $C_1$-$C_6$ alkyl, $C_3$-$C_6$ cycloalkyl, allyl, substituted or unsubstituted $C_1$-$C_6$ alkoxy, aryl, or amino;
$R_4$ is H, substituted or unsubstituted $C_1$-$C_6$ alkyl, $C_3$-$C_6$ cycloalkyl or allyl;
$R_7$ is H or substituted or unsubstituted $C_1$-$C_6$ alkyl, $C_3$-$C_6$ cycloalkyl or allyl;
$R_8$ and $R_9$ are each independently H, substituted or unsubstituted $C_1$-$C_6$ alkyl, $C_3$-$C_6$ cycloalkyl or allyl; or $R_8$ and $R_9$, together with the nitrogen atom to which they are attached, form a 4-10-membered heterocyclic ring; and
n is 0 to 4;
or a pharmaceutically acceptable salt or solvate thereof.

2. The method of claim 1, wherein $R_4$ is H or methyl.
3. The method of claim 1, wherein $R_1$ is methyl or ethyl.
4. The method of claim 1, wherein $R_2$ is methyl or ethyl.
5. The method of claim 1, wherein the compound is a compound of formula (I) and n is one or two and each $R_3$ is methyl.
6. The method of claim 1, wherein the compound is a compound of formula (I) and n is at least 3, and two occurrences of $R_3$ are gem-dimethyl groups and one occurrence of $R_3$ is oxo.
7. The method of claim 1, wherein the compound is a compound of formula (II) and $R_8$ is H and $R_9$ is —(CH$_2$)$_2$N(ethyl)$_2$.

8. The method of claim 1, wherein the compound is selected from the group consisting of:

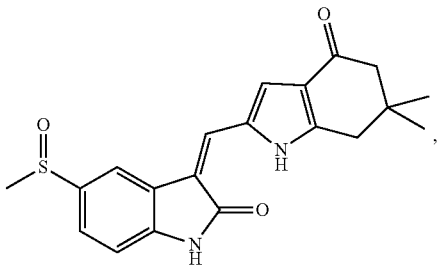

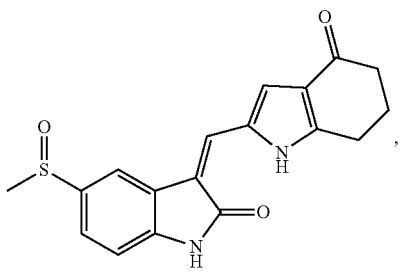

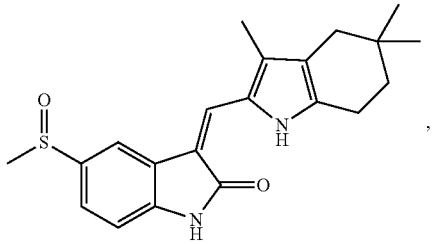

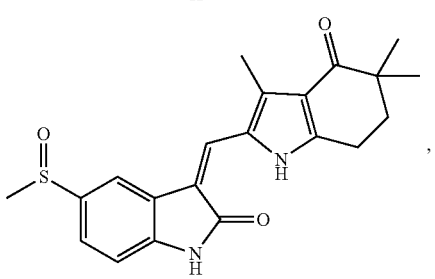

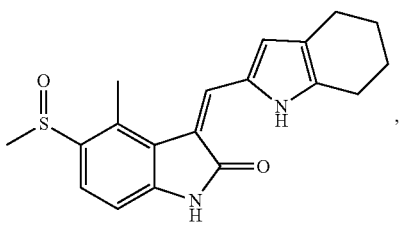

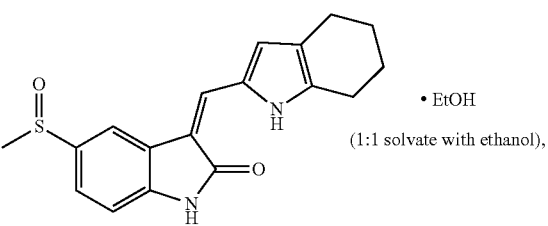

(1:1 solvate with ethanol),

-continued

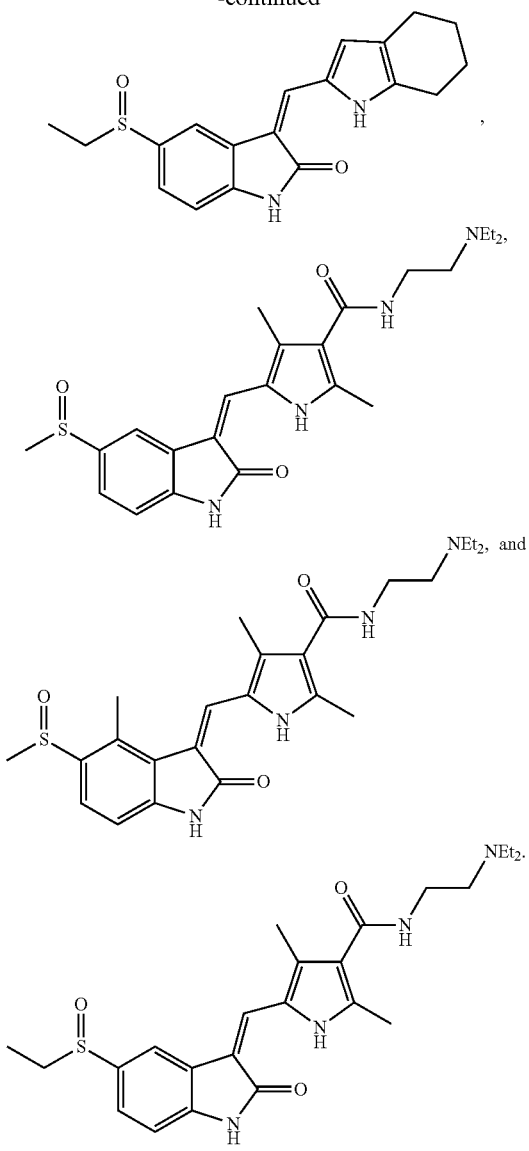

9. The method of claim 1, wherein the macular degeneration is wet macular degeneration.

10. The method of claim 1, wherein the macular degeneration is dry macular degeneration.

11. The method of claim 1, wherein the step of administering the compound includes administering the compound in a pharmaceutically acceptable composition.

12. The method of claim 1, wherein the subject is a mammal.

13. The method of claim 1, wherein the subject is a human.

14. The method of claim 1, further comprising the step of monitoring the subject to determine the efficacy of treatment.

15. The method of claim 1, wherein the effective amount of the compound of claim 1, or a pharmaceutically acceptable salt thereof, is in a range of 0.0001 to about 100 mg per kilogram of body weight per day.

16. The method of claim 1, wherein the compound of formula (I) or formula (II), or pharmaceutically acceptable salt or solvate thereof, is administered to the subject by a method selected from the group consisting of: oral, topical, parenteral, and systemic.

17. The method of claim 1, wherein the macular degeneration involves degeneration, dysfunction, or loss of retinal ganglion cells.

18. The method of claim 1, wherein the compound of formula (I) or formula (II) promotes survival and/or neurite outgrowth of retinal ganglion cells.

19. The method of claim 1, further comprising administering an additional therapeutic agent to the subject, wherein the additional therapeutic agent is selected from the group consisting of beta-blockers, alpha-agonists, carbonic anhydrase inhibitors, prostaglandins or prostaglandin analogs, miotic or cholinergic agents, epinephrine compounds, forskolin, or neuroprotective compounds.

20. A kit comprising a compound of formula (I) or formula (II), or a pharmaceutically acceptable salt or solvate thereof, in unit dosage form, together with instructions for using the compound, or a pharmaceutically acceptable salt or solvate thereof, for therapeutically treating macular degeneration, wherein the compound of formula (I) or formula (II) comprises:

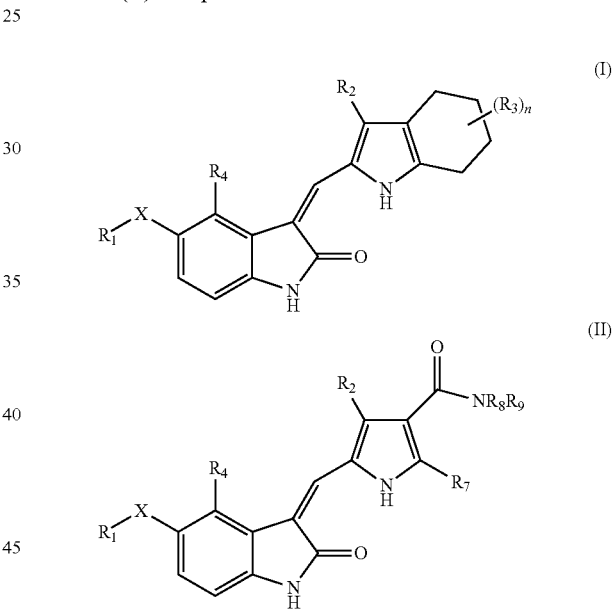

wherein:
X is S(O);
$R_1$ is substituted or unsubstituted $C_1$-$C_6$ alkyl, $C_3$-$C_6$ cycloalkyl or allyl;
$R_2$ is H or substituted or unsubstituted $C_1$-$C_6$ alkyl, $C_3$-$C_6$ cycloalkyl or allyl;
$R_3$ is selected, independently for each occurrence, from the group consisting of substituted or unsubstituted $C_1$-$C_6$ alkyl, $C_3$-$C_6$ cycloalkyl, allyl, substituted or unsubstituted $C_1$-$C_6$ alkoxy, aryl, cyano, halogen, hydroxy, oxo, amino, or —C(O)—$R_a$, in which $R_a$ is substituted or unsubstituted $C_1$-$C_6$ alkyl, $C_3$-$C_6$ cycloalkyl, allyl, substituted or unsubstituted $C_1$-$C_6$ alkoxy, aryl, or amino;
$R_4$ is H, substituted or unsubstituted $C_1$-$C_6$ alkyl, $C_3$-$C_6$ cycloalkyl or allyl;
$R_7$ is H or substituted or unsubstituted $C_1$-$C_6$ alkyl, $C_3$-$C_6$ cycloalkyl or allyl;

$R_8$ and $R_9$ are each independently H, substituted or unsubstituted $C_1$-$C_6$ alkyl, $C_3$-$C_6$ cycloalkyl or allyl; or $R_8$ and $R_9$, together with the nitrogen atom to which they are attached, form a 4-10-membered heterocyclic ring; and n is 0 to 4.

21. The kit of claim 20, wherein the macular degeneration is wet macular degeneration.

22. The kit of claim 20, wherein the macular degeneration is dry macular degeneration.

23. The kit of claim 20, wherein the macular degeneration involves degeneration, dysfunction, or loss of retinal ganglion cells.

24. The kit of claim 20, wherein the compound of formula (I) or formula (II) promotes survival and/or neurite outgrowth of retinal ganglion cells.

25. The kit of claim 20, further comprising an additional therapeutic agent, wherein the additional therapeutic agent is selected from the group consisting of beta-blockers, alpha-agonists, carbonic anhydrase inhibitors, prostaglandins or prostaglandin analogs, miotic or cholinergic agents, epinephrine compounds, forskolin, or neuroprotective compounds.

* * * * *

UNITED STATES PATENT AND TRADEMARK OFFICE
CERTIFICATE OF CORRECTION

| | | |
|---|---|---|
| PATENT NO. | : 9,539,239 B1 | Page 1 of 1 |
| APPLICATION NO. | : 14/886938 | |
| DATED | : January 10, 2017 | |
| INVENTOR(S) | : Donald Jeffrey Zack et al. | |

It is certified that error appears in the above-identified patent and that said Letters Patent is hereby corrected as shown below:

In the Specification

Column 1, please replace the second paragraph as follows:
STATEMENT OF GOVERNMENTAL INTEREST
This invention was made with government support under grant number EY019737, awarded by the National Institutes of Health. The government has certain rights in the invention.

Signed and Sealed this
Twentieth Day of March, 2018

Andrei Iancu
*Director of the United States Patent and Trademark Office*